(12) United States Patent
Lindsley et al.

(10) Patent No.: US 7,427,472 B2
(45) Date of Patent: Sep. 23, 2008

(54) METHODS FOR THE DIFFERENTIATION AND IDENTIFICATION OF MEDICALLY IMPORTANT ENDEMIC FUNGI

(75) Inventors: Mark D. Lindsley, Lawrenceville, GA (US); Zhenyu Qin, Atlanta, GA (US); Christine J. Morrison, Decatur, GA (US); Jong S. Choi, Daegu (KR)

(73) Assignee: United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 439 days.

(21) Appl. No.: 10/490,726

(22) PCT Filed: Sep. 25, 2002

(86) PCT No.: PCT/US02/30605

§ 371 (c)(1),
(2), (4) Date: Mar. 24, 2004

(87) PCT Pub. No.: WO03/027329

PCT Pub. Date: Apr. 3, 2003

(65) Prior Publication Data

US 2005/0260584 A1 Nov. 24, 2005

Related U.S. Application Data

(60) Provisional application No. 60/325,241, filed on Sep. 26, 2001.

(51) Int. Cl.
*C12Q 1/68* (2006.01)
*C12P 19/34* (2006.01)
*C07H 21/04* (2006.01)

(52) U.S. Cl. ............... 435/6; 435/91.2; 536/24.32; 536/24.33

(58) Field of Classification Search ............... None
See application file for complete search history.

(56) References Cited

U.S. PATENT DOCUMENTS 5,426,027 A 6/1995 Lott et al.

(Continued)

FOREIGN PATENT DOCUMENTS

| WO | WO 98/50584 | 11/1998 |
| WO | WO 99/06596 A1 | 2/1999 |
| WO | WO 01/96612 A2 | 12/2001 |
| WO | WO 01/96612 A3 | 12/2001 |

OTHER PUBLICATIONS

White, T.J. et al. Amplification and direct sequencing of fungal ribosomal RNA genes for phylogenetics. Chapter 38 in "PCR Protocols: A Guide to Methods and Applications," Innis, M.A. et al, eds., Academic Press, Inc., San Diego, 1990.*

(Continued)

*Primary Examiner*—Diana B Johannsen
(74) *Attorney, Agent, or Firm*—Klarquist Sparkman, LLP

(57) ABSTRACT

Methods of detecting a dimorphic fungus, including differentiating a dimorphic fungus from other fungi are disclosed. A sample suspected of containing a nucleic acid of a fungus, such as an internal transcribed spacer-2 (ITS2) nucleic acid sequence of a dimorphic fungal rDNA, is screened for the presence or absence of that nucleic acid. The presence of the nucleic acid indicates the sample was contacted by the fungus. Determining whether the nucleic acid sequence is present in the sample can be accomplished by detecting hybridization between a dimorphic probe, species-specific probe, and/or microbe-specific probe and a nucleic acid sequence corresponding to the ITS2 region of fungal rDNA. Kits and arrays for carrying out these methods also are disclosed.

34 Claims, 9 Drawing Sheets

U.S. PATENT DOCUMENTS

| | | | |
|---|---|---|---|
| 5,631,132 | A | 5/1997 | Lott et al. |
| 5,635,353 | A | 6/1997 | Lott et al. |
| 5,645,992 | A | 7/1997 | Lott et al. |
| 5,955,274 | A | 9/1999 | Ligon et al. |
| 6,235,890 | B1 | 5/2001 | Morrison et al. |

OTHER PUBLICATIONS

Lazar, J.G. Advanced methods in PCR product detection. PCR Methods and Applications, Manual Supplement, Cold Spring Harbor Laboratory 1994, pp. S1-S14.*

Elie et al., "Rapid Identification of *Candida* Species with Species-Specific DNA Probes," *J. Clin. Microbiol.* 36:3260-3265 (1998).

Reiss et al., "Molecular Diagnosis and Epidemiology of Fungal Infections," *Med. Mycol.* 36:249-257 (1998).

Turenne et al., "Rapid Identification of Fungi by Using the ITS2 Genetic Region and an Automated Fluorescent Capillary Electrophoresis System," *J. Clin. Microbiol.* 37:1846-1851 (1999).

Caligiorne et al., "Dematiaceous Fungal Pathogens: Analysis of Ribosomal DNA Gene Polymorphism by Polymerase Chain Reaction-Restriction Fragment Length Polymorphism," *Mycoses* 42:609-614 (1999).

Gaskell et al., "Analysis of the Internal Transcribed Spacer Regions of Ribosomal DNA in Common Airborne Allergenic Fungi," *Electrophoresis* 18:1567-1569 (1997).

Hendolin et al., "Panfungal PCR and Multiplex Liquid Hybridization for Detection of Fungi in Tissue Specimens," *J. Clin. Microbiol.* 38:4186-4192 (2000).

Henry et al., "Identification of *Aspergillus* Species Using Internal Transcribed Spacer Regions 1 and 2," *J. Clin. Microbiol.* 38:1510-1515 (2000).

Hershkovitz and Lewis, "Deep-Level Diagnostic Value of the rDNA-ITS Region," *Mol. Biol. Evol.* 13:1276-1295 (1996).

Lindsley et al., 35th *Annual Meeting of the Infectious Diseases Society of America*, Abstract 28, p. 76 (1997).

Lindsley et al., 40th *Interscience Conference on Antimicrobial Agents and Chemotherapy* Abstract 1335, p. 378 (2000).

Lindsley et al., "Rapid Identification of Dimorphic and Yeast-Like Fungal Pathogens Using Specific DNA Probes," *J. Clin. Microbiol.* 39:3505-3511 (2001).

O'Donnell and Cigelnik, "Two Divergent Intragenomic rDNA ITS2 Types Within a Monophyletic Lineage of the Fungus *Fusarium* Are Nonorthologous," *Mol. Phylogenet. Evol.* 7:103-116 (1997).

Ruiz-Díez and Martinez-Suárez, "Electrotransformation of the Human Pathogenic Fungus *Scedosporium prolificans* Mediated by Repetitive rDNA Sequences," *FEMS Immunol. Med. Microbiol.* 25:275-282 (1999).

Choi et al., 98th *General Meeting of the American Society for Microbiology*, Abstract C288, p. 179, 1998.

Elie et al., 98th *General Meeting of the American Society for Microbiology*, Abstract C290, p. 179, 1998.

Fujita et al., *J. Clin. Microbiol.* 33:962-967, 1995.

Jiang et al., *J. Clin. Microbiol.* 38(1):241-245, 2000.

Lobuglio and Taylor, *J. Clin. Microbiol.* 33(1):85-89, 1995.

Lott et al., *Yeast* 9:1199-1206, 1993.

Qin et al., 41st *Interscience Conference on Antimicrobial Agents and Chemotherapy*, Paper No. 838, "Rapid Differentiation of *Penicillium marneffei* from Other Fungi Using Species-Specific DNA Probes," 2001.

Qin and Morrison, 41st *Interscience Conference on Antimicrobial Agents and Chemotherapy*, Paper No. 849, "High-Throughput Fungal DNA Mini Preparations for Use in PCT-Based Applications," 2001.

Skolnick, *J.A.M.A.* 275(8):581-582, 1996.

Vanittanakom et al., *Med. Mycol.* 36:169-175, 1998.

White et al., *PCR Protocols: A Guide to Methods and Applications*, Chapter 38, p. 315-322, Academic Press, Inc., 1990.

Database GenEMbl Accession No. L37406, Lobuglio et al., Feb. 1996.

Database GenEmbl Accession No. AF129543, Jiang et al., Jan. 2000.

\* cited by examiner

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Universal forward primer

<400> SEQUENCE: 1
tccgtaggtg aacctgcgg                                                    19

<210> SEQ ID NO 2
<211> LENGTH: 20
<212> TYPE: DNA
<213> ORGANISM: Artificial Sequence
<220> FEATURE:
<223> OTHER INFORMATION: Universal reverse primer

<400> SEQUENCE: 2
tcctccgctt attgatatgc                                                   20

<210> SEQ ID NO 3
<211> LENGTH: 20
<212> TYPE: DNA
<213> ORGANISM: Artificial Sequence
<220> FEATURE:
<223> OTHER INFORMATION: Universal capture probe

<400> SEQUENCE: 3
gcatcgatga agaacgcagc                                                   20

<210> SEQ ID NO 4
<211> LENGTH: 25
<212> TYPE: DNA
<213> ORGANISM: Artificial Sequence
<220> FEATURE:
<223> OTHER INFORMATION: Probe for all endemic dimorphic fungi

<400> SEQUENCE: 4
ggacgtgccc gaaatgcagt ggcgg                                             25

<210> SEQ ID NO 5
<211> LENGTH: 29
<212> TYPE: DNA
<213> ORGANISM: Artificial Sequence
<220> FEATURE:
<223> OTHER INFORMATION: Probe for Histoplasma capsulatum

<400> SEQUENCE: 5
accatctcaa cctcctttt cacaccagg                                          29

<210> SEQ ID NO 6
<211> LENGTH: 21
<212> TYPE: DNA
<213> ORGANISM: Artificial Sequence
<220> FEATURE:
<223> OTHER INFORMATION: Probe for Blastomyces dermatitidis

<400> SEQUENCE: 6
ggtcttcggg ccggtctccc c 21

<210> SEQ ID NO 7
<211> LENGTH: 20

```
<212> TYPE: DNA
<213> ORGANISM: Artificial Sequence
<220> FEATURE:
<223> OTHER INFORMATION: Probe for Coccidioides immitis

<400> SEQUENCE: 7
ctcttttttt tattatatcc                                              20

<210> SEQ ID NO 8
<211> LENGTH: 16
<212> TYPE: DNA
<213> ORGANISM: Artificial Sequence
<220> FEATURE:
<223> OTHER INFORMATION: Probe for Paracoccidioides brasiliensis

<400> SEQUENCE: 8
cactcatgga ccccgg                                                  16

<210> SEQ ID NO 9
<211> LENGTH: 18
<212> TYPE: DNA
<213> ORGANISM: Artificial Sequence
<220> FEATURE:
<223> OTHER INFORMATION: Probe for Sporothrix schenckii

<400> SEQUENCE: 9
gacgcgcagc tcttttta                                                18

<210> SEQ ID NO 10
<211> LENGTH: 18
<212> TYPE: DNA
<213> ORGANISM: Artificial Sequence
<220> FEATURE:
<223> OTHER INFORMATION: Probe for Penicillium marneffei

<400> SEQUENCE: 10
gggttggtca ccaccata                                                18

<210> SEQ ID NO 11
<211> LENGTH: 19
<212> TYPE: DNA
<213> ORGANISM: Artificial Sequence
<220> FEATURE:
<223> OTHER INFORMATION: Probe for Cryptococcus neoformans

<400> SEQUENCE: 11
cctatggggt agtcttcgg                                               19

<210> SEQ ID NO 12
<211> LENGTH: 20
<212> TYPE: DNA
<213> ORGANISM: Artificial Sequence
<220> FEATURE:
<223> OTHER INFORMATION: Probe for Pneumocystis carinii

<400> SEQUENCE: 12
gtagtagggt taattcaatt                                              20
```

METHODS FOR THE DIFFERENTIATION AND IDENTIFICATION OF MEDICALLY IMPORTANT ENDEMIC FUNGI

CROSS-REFERENCE TO RELATED APPLICATION

This is a national stage under 35 U.S.C. §371 of International Application No. PCT/US02/30605 filed Sep. 25. 2002, and claims the benefit of U.S. Provisional Patent Application No. 60/325,214, filed on Sep. 26, 2001.

FIELD

This invention relates to molecular identification of fungi, including methods of identifying fungi based on unique genetic characteristics, such as using nucleic acid probes to detect the presence of and identify nucleotides obtained from species and classes of fungi.

BACKGROUND

The incidence of disease caused by pathogenic and opportunistic fungi has been increasing over the past decade. See, e.g., McNeil, M. M, et al., Clin. Infect. Dis. 33:641-47 (2001); Ampel, N. M., et al., Clin. Infect. Dis. 27:1528-30 (1998); National Nosocomial Infections Surveillance (NNIS) System report, data summary from Jan. 1990 to May 1999, Am. J. Infect. Control 27:520-32 (1999). In humans, these fungal infections are especially prevalent in people with suppressed immune systems, such as HIV-positive and severely ill patients. For example, *Penicillium marneffei* is the third most common cause of opportunistic infections in patients with AIDS in Thailand. Vanittanakom N., Sirisanthana T., Curr. Top. Med. Mycol. 8:3542 (1997). Additionally, *P. chrysogenum* and *P. citrinum* have been recognized as the cause of human disease.

Diagnosis of fungal infections is typically made by isolating the infective organism in culture, by serologic assays, or through histopathologic examination of tissue. See, e.g., Hamilton, A. J., Med. Mycol. 36:351-64 (1998). However, pathogenic fungi may require several weeks to grow, and a positive culture may represent benign colonization, rather than true invasion and infection, especially when opportunistic organisms are isolated. Serologic tests on a single serum sample to detect circulating antifungal antibodies may be inconclusive (especially in immunosuppressed subjects). The acquisition of paired acute and convalescent sera, which is necessary for a definitive serologic diagnosis, requires an additional 3 to 4 weeks before convalescent serum can be obtained. Morrison C. J., and Lindsley, M. D., in Fungal Pathogenesis: Principles and Clinical Applications (New York: Marcel Dekker Inc., 2001; Calderone R. A., and Cihlar R. L., eds.). Therefore, histopathologic examination of tissue sections was often the most rapid, and sometimes the only, method available to diagnose invasive fungal disease. However, histopathologic diagnosis of fungal infections is usually made through morphologic criteria, and fungi with atypical morphologic features can be difficult to identify and diagnose. In addition, fungi for which different anti-fungal therapies could be used often look morphologically similar in tissue sections.

The relatively recent development of automated DNA synthesis has allowed production of molecular probes with consistently defined properties that may result in increased test sensitivity, specificity, and reproducibility. Past research in the molecular identification of fungi has typically concentrated on a single species or genus of a fungus. See, e.g., LoBuglio, K. F., and J. W. Taylor, J. Clin. Microbiol. 33:85-89 (1995); Loffler, J., et al., Med. Mycol. 36:275-79 (1998). For example, U.S. Pat. Nos. 5,631,132; 5,426,027; 5,635,353; and 5,645,992; and PCT publication WO 98/50584, disclose nucleic acid probes and methods for detecting fungal species based on a certain region (the ITS2 region) of rDNA. Additionally, some methods of molecular identification of fungi can be very difficult or cumbersome to perform, or require expensive, specialized equipment. See, e.g., Sandhu, G. S., et al., J. Clin. Microbiol. 35:1894-96 (1997); Sandhu, G. S., et al., J. Clin. Microbiol. 33:2913-19 (1995); and Turenne, C. Y., et al., J. Clin. Microbiol. 37:1846-51 (1999).

SUMMARY

Disclosed is a method of detecting a dimorphic fungus, including a method of differentiating the dimorphic fungus from non-dimorphic fungi, including fungi of the same biological genus.

In some embodiments, a sample suspected of containing a nucleic acid of a fungus, such as an internal transcribed spacer-2 (ITS2) nucleic acid sequence of a dimorphic fungal rDNA, is screened for the presence or absence of that nucleic acid. Any suitable sample, including a biological sample (e.g., blood, sputum, bronchoalveolar levage, or biopsied tissue) can be used, and the nucleic acid can be amplified within the sample, such as by the polymerase chain reaction (PCR). In particular embodiments, the nucleic acid is detected and identified by a polymerase chain reaction enzyme-immunoassay (PCR-EIA). The presence of the nucleic acid indicates the sample was contacted by the fungus, such as samples presently containing the fungus. The dimorphic fungi include, but are not limited to, *Histoplasma capsulatum, Blastomyces dermatitidis, Coccidioides immitis, Paracoccidioides brasiliensis*, and *Penicillium marneffei*.

If PCR is used to amplify the nucleic acid in the sample, an ITS1 or ITS4 primer (listed in SEQ ID NO: 1 and SEQ ID NO: 2) can be used. While the ITS3 sequence (SEQ ID NO: 3) can be used as a probe, ITS3 also can be used as a PCR primer for amplifying the ITS2 region.

A sample can be prepared by processing and extracting nucleic acids from a sample. In some embodiments, a high-throughput DNA extraction technique is used to extract DNA from fungal cells. In particular embodiments, a mixture of plural types of glass microspheres differentiated by size (e.g., diameters of about 106 μm, about 0.5 mm; and about 3 mm) or differentiated according to a particular size ratio (e.g., a size ratio of a first microsphere to a second microsphere of about 1:5, a size ratio of the second microsphere to a third microsphere of about 1:6, and a size ratio of the first microsphere to the third microsphere of about 1:30) can be used. Alternatively, the ratio of diameters of the spheres is about 0.1 to 0.5 to 3.0.

Determining whether the nucleic acid sequence is present in the sample can be accomplished by a variety of techniques. In some embodiments, a probe is hybridized to an ITS2 nucleic acid, with detection of hybridization indicating that the ITS2 nucleic acid is present in the sample (and that the sample came into contact with a dimorphic fungus). In particular embodiments, the probe comprises at least 15 contiguous nucleotides, such as at least 20 contiguous nucleotides, of the following probe sequences: Dm (SEQ ID NO: 4), Hc (SEQ ID NO: 5), Bd (SEQ ID NO:6), Ci (SEQ ID NO: 7), Pb (SEQ ID NO: 8), or Pm (SEQ ID NO: 10). In more particular embodiments, the probe consists essentially of one these sequences, such as Dm.

The probe can hybridize a segment of the ITS2 nucleic acid, such as a particular half, third, quarter, or other subdivision of the ITS2 region. In some embodiments, the probe hybridizes to a portion of the ITS2 sequence beginning at about nucleotide 40 to 55, such as about nucleotide 44, 45, or 51, numbered after the end of the 5.8S coding sequence and extending downstream for the length of the probe.

In some embodiments, the method is capable of differentiating a dimorphic fungus from a second dimorphic or non-dimorphic fungus, such as *Sporothrix schenckii, Cryptococcus neoformans*, a *Candida* species, or *Pneumocystis carinii*. In particular embodiments, the method is capable of differentiating *Penicillium marneffei* from *Penicillium camembertii, Penicillium caseicolum, Penicillium chrysogenum, Penicillium glabrum, Penicillium griseofulvum, Penicillium italicum, Penicillium janthinellum, Penicillium purpurescens, Penicillium citrinum, Penicillium purpurogenum, Penicillium roquefortii, Penicillium rubefaciens, Penicillium spinulosum, Sporothrix schenckii, Cryptococcus neoformans*, a *Candida* species, an *Aspergillus* species, a *Fusarium* species, a *Mucor* species, a *Rhizopus* species, or *Pneumocystis carinii*.

Kits and arrays for carrying out these methods also are disclosed.

BRIEF DESCRIPTION OF THE DRAWINGS

FIGS. 3A and 3B illustrate a sequence alignment indicating the dimorphic probe (Dm) of several fungal species and the locations of microbe-specific probes (SEQ ID NOS: 13-21).

SEQUENCE LISTING

Figure 1A:
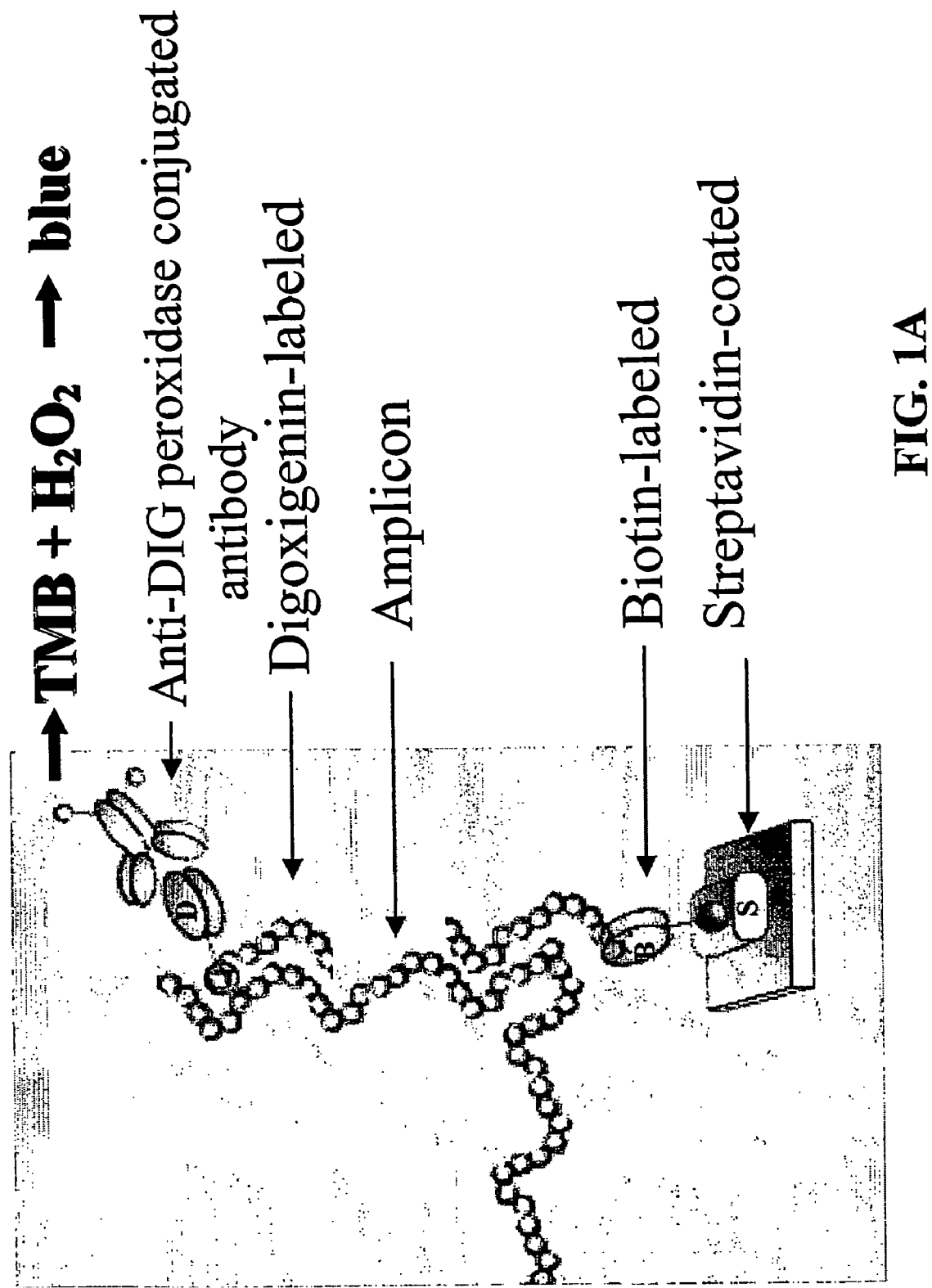
FIGS. 1A and 1B illustrate a generalized polymerase chain reaction-enzyme immunoassay (PCR-EIA) method.

The nucleic acid sequences listed in the accompanying sequence listing are shown using standard letter abbreviations for nucleotide bases. Only one strand of each nucleic acid sequence is shown, but the complementary strand is understood as included by reference to the displayed strand.

SEQ ID NO: 1 shows the nucleic acid sequence of fungal universal forward primer ITS1.

SEQ ID NO: 2 shows the nucleic acid sequence of fungal universal reverse primer ITS4.

SEQ ID NO: 3 shows the nucleic acid sequence of fungal universal capture probe or forward primer ITS3.

SEQ ID NO: 4 shows the nucleic acid sequence of a probe for endemic dimorphic fungi.

SEQ ID NO: 5 shows the nucleic acid sequence of a probe to the ITS2 region of *Histoplasma capsulatum*.

SEQ ID NO: 6 shows the nucleic acid sequence of a probe to the ITS2 region of *Blastomyces dermatitidis*.

SEQ ID NO: 7 shows the nucleic acid sequence of a probe to the ITS2 region of *Coccidioides immitis*.

SEQ ID NO: 8 shows the nucleic acid sequence of a probe to the ITS2 region of *Paracoccidioides brasiliensis*.

SEQ ID NO: 9 shows the nucleic acid sequence of a probe to the ITS2 region of *Sporothrix schenckii*.

SEQ ID NO: 10 shows the nucleic acid sequence of a probe to the ITS2 region of *Penicillium marneffei*.

SEQ ID NO: 11 shows the nucleic acid sequence of a probe to the ITS2 region of *Cryptococcus neoformans*.

SEQ ID NO: 12 shows the nucleic acid sequence of a probe to the ITS2 region of *Pneumocystis carinii*.

SEQ ID NO: 13 shows the nucleic acid sequence of a probe to the ITS2 region of *Penicillium citrinum*.

SEQ ID NO: 14 shows the nucleic acid sequence of a probe to the ITS2 region of *Penicillium purpurogenum*.

DETAILED DESCRIPTION

Explanation of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a dimorphic probe" means "including a dimorphic probe" without excluding other elements.

The term "or" refers to a single element of stated alternative elements or a combination of two or more elements. For example, the phrase "the probe comprising 15 contiguous nucleotides of SEQ ID NO: 4 or SEQ ID NO: 10 refers to a probe comprising 15 contiguous nucleotides of SEQ ID NO: 4, a probe comprising 15 contiguous nucleotides of SEQ ID NO: 10, or a probe comprising 15 contiguous nucleotides of SEQ ID NO: 4 and 15 contiguous nucleotides of SEQ ID NO: 10.

In order to facilitate review of the various embodiments of the invention, the following explanations of terms are provided:

Amplification: of a nucleic acid molecule (e.g., a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

The amplification method can be modified in certain embodiments, including for example modification by additional steps or coupling the amplification with another protocol. For example, as described in Example 8, a polymerase chain reaction-enzyme immunoassay (PCR-EIA) method can be used for amplification and differentiation of fungi. Such a PCR-EIA method is described in Elie, C. M., et al., J. Clin. Microbiol. 36:3260-65 (1998); and Fujita, S., et al., J. Clin. Microbiol. 33:962-67 (1995), and this PCR-EIA method can be modified to suit particular embodiments.

Figure 1B:
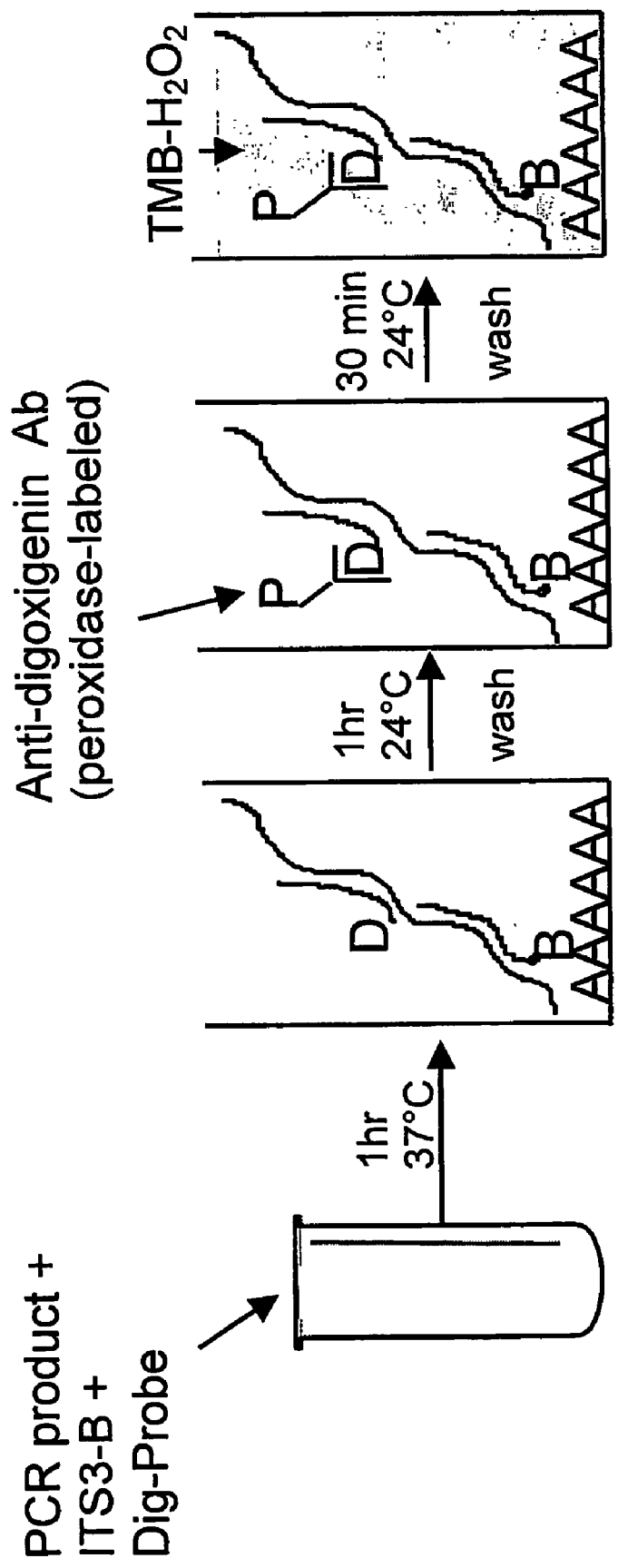

FIGS. 1A-B illustrate a generalized PCR-EIA method. Denatured amplicons are hybridized with a biotin-labeled capture probe (B) and a digoxigenin-labeled detection probe (D) in an Eppendorf® tube before addition to wells of a streptavidin-coated microtiter plate (S). Horseradish peroxidase-conjugated anti-digoxigenin antibody is then added, and amplicons bound to the wells are detected colorimetrically at $A_{650nm}$ after addition of TMB-$H_2O_2$ substrate.

Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in 5,427,930; and NASBA™ RNA transcription-free amplification, as disclosed in U.S. Pat. No. 6,025,134.

Animal: A living multi-cellular vertebrate or invertebrate organism, a category that includes, for example, mammals and birds. The term mammal includes both human and non-human mammals. Similarly, the term "subject" includes both human and veterinary subjects.

Sample: Encompasses a sample obtained from an animal, plant, or the environment. An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs.

A "biological sample" is a sample obtained from a plant or animal subject. As used herein, biological samples include all clinical samples useful for detection of microbial or fungal infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; bronchoalveolar levage (BAL); and saliva. In particular embodiments, the biological sample is obtained from an animal subject, such as blood, serum, cerebrospinal fluid, BAL, pus, or prostate fluid.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from messenger RNA extracted from cells.

Dimorphic: "Dimorphic," or "thermally dimorphic," describes a class of fungi that demonstrate two different, temperature dependent morphologies in their life cycles. At room temperature (about 25° C.), dimorphic fungi live in a mold-like phase, including growing hyphae. At body temperature (about 37° C.), dimorphic fungi demonstrate a yeast-like phase by forming yeast-like cells.

The endemic dimorphic fungi include, but are not limited to, the following genera and species: *Histoplasma capsulatum*, *Blastomyces dermatitidis*, *Coccidioides immitis*, *Paracoccidioides brasiliensis*, and *Penicillium marneffei*. Other dimorphic fungi include, but are not limited to, *Sporothrix schenkii* and *Candida* species.

Fungus: Living, single-celled and multicellular organisms belonging to Kingdom Fungi. Most species are characterized by a lack of chlorophyll and presence of chitinous cell walls, and some fungi can be multinucleated. Representative, non-limiting examples of fungi include the genera and species listed in Tables 2, 3, and 5-8 below, such as *Histoplasma capsulatum*, *Blastomyces dermatitidis*, *Coccidioides immitis*, *Paracoccidioides brasiliensis*, *Penicillium marneffei*, *Sporothrix schenckii*, *Cryptococcus neoformans*, *Candida* species, *Fusarium* species, *Rhizopus* species, *Aspergillus* species, *Mucor* species, and *Pneumocystis carinii*.

Homolog: A nucleotide sequence that shares a common ancestor with another nucleotide sequence; the homologs diverged when a species carrying that ancestral sequence split into two species.

Isolated: An "isolated" microorganism (such as a bacteria, fungus, or protozoan) has been substantially separated or purified away from microorganisms of different types, strains, or species. For example, a colony of *Penicillium marneffei* would be considered an "isolated" *Penicillium marneffei*. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Figure 2:
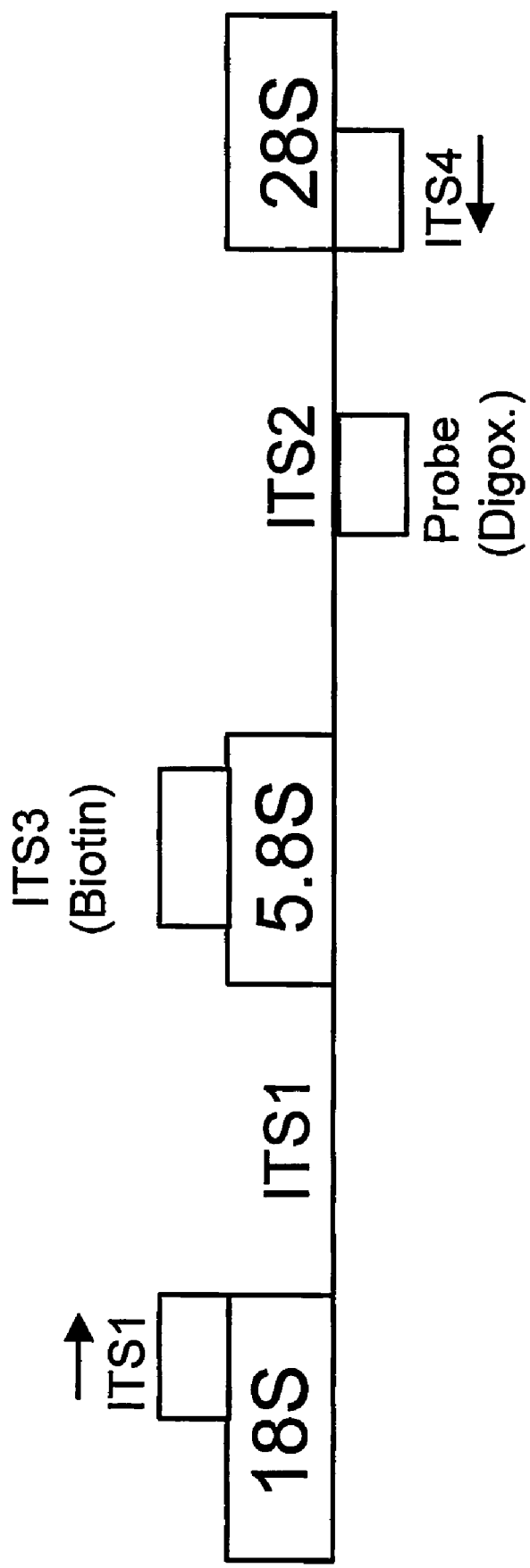
FIG. 2 is a diagram of fungal rDNA, including the hybridization sites of primers and probes.

ITS2: An internal transcribed spacer sequence of fungal rDNA. As illustrated in FIG. 2, a diagram of the fungal rDNA region, the ITS2 sequence is located between the 5.8S and 28S coding sequences. Additionally, hybridization sites for the ITS1 and ITS4 primers are shown in the phylogenetically conserved 18S and 28S rDNA regions, with arrows designating the direction of amplification (ITS1 is a forward primer, while ITS4 is a reverse primer). ITS3 (Biotin) represents the biotinylated, universal fungal probe that binds in the phylogenetically-conserved, 5.8S rDNA region. However, non-biotynilated ITS3 also can be used as a forward primer. Probe (Digox.) represents digoxigenin-labeled, species-specific probes which bind to the less highly conserved, ITS2 region, for example (and without limitation) the probes listed in Table 1 below.

Oligonucleotide: A linear polynucleotide sequence of between 5 and 100 nucleotide bases in length.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Probes and primers: Nucleic acid probes and primers can be readily prepared based on the nucleic acid molecules provided in this invention. A probe comprises an isolated nucleic acid capable of hybridizing to a template nucleic acid, and a detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed in, for example, Sambrook et al. (Molecular Cloning: A Laboratory Manual (Cold Spring Harbor Laboratory Press, Cold Spring Harbor, N.Y., 2001)) and Ausubel et al., eds. (Short Protocols in Molecular Biology (John Wiley and Sons, New York, N.Y., 1999).

Primers are short nucleic acid molecules, for example DNA oligonucleotides 15 nucleotides or more in length. Primers can be annealed to a complementary target DNA strand by nucleic acid hybridization to form a hybrid between the primer and the target DNA strand, and the primer can be extended along the target DNA strand by a DNA polymerase enzyme. Primer pairs can be used for amplification of a nucleic acid sequence, e.g., by the polymerase chain reaction (PCR) or other nucleic acid amplification methods.

Methods for preparing and using probes and primers are described, for example, in Sambrook et al.; Ausubel et al., eds.; and Innis et al. (PCR Applications, Protocols for Functional Genomics (Academic Press, Inc., San Diego, Calif., 1999)). PCR primer pairs can be derived from a known sequence, for example, by using computer programs intended for that purpose such as Primer3 (Whitehead Institute for Biomedical Research, Cambridge, Mass.; this program is accessible through the Whitehead Institute's website).

The specificity of a particular probe or primer increases with its length. Thus, as one non-limiting example, a primer comprising 15 consecutive nucleotides of the *P. marneffei* ITS2 sequence will anneal to a target sequence, such as another ITS2 homolog from the family contained within a *P. marneffei* genomic DNA library, with a higher specificity than a corresponding primer of only 10 nucleotides; thus, in order to obtain greater specificity, probes and primers can be selected that comprise 10, 15, 20, 25, 30, 35, 40, 50, 75, 100, or more consecutive nucleotides of *P. marneffei* ITS2 sequences.

Included are isolated nucleic acid molecules (such as probes and primers) that comprise specified lengths of a fungal ITS2 sequence. Such molecules can comprise at least 10, 15, 20, 25, 30, 35, 40, 50, 75, 100, or more consecutive nucleotides of the ITS2 sequence, and can be obtained from any region of the ITS2 sequence. In some embodiments, the ITS2 region is subdivided into smaller parts, such as halves, thirds, quarters, fifths, sixths, tenths, or twentieths. In particular embodiments, these divided portions are numbered sequentially beginning with the portion adjacent the 5.8S coding region. By way of example only, an ITS2 sequence can be apportioned into halves, thirds, or quarters based on sequence length, and the isolated nucleic acid molecules can be derived from the first or second halves of the molecules, any of the three thirds of the molecules, or any of the four quarters of the molecules.

The generalized ITS2 sequence is diagrammed in FIG. 2, and ITS2 sequences for particular fungi can be cloned and sequenced using standard techniques (e.g., as described in Sambrook et al.) or obtained from public or private sequence databases, such as GenBank. Particular sequences are listed in Table 1 and the accompanying sequence listing.

The fungal sequence amplified by the ITS1 and ITS4 primers is generally about 600 nucleotides in length and can be hypothetically divided into about halves (e.g., nucleotides 1 to about 300 and about 301 to about 600) or about quarters (e.g., nucleotides 1 to about 150, about 151 to about 300, about 301 to about 450, and about 451 to about 600), for instance. However, as stated above, other divisions into segments are possible, such as tenths, fifths, sixths, and eighths. Additionally, any particular portion of the ITS2 region can be identified with reference to particular nucleotides, for example (and without limitation) nucleotides 1-55, 40-95, 70-130, 83-157, 200-425, or 315 to 600.

As illustrated in FIG. 2, the ITS2 region is located between the 5.8S and 28S coding sequences of fungal rDNA. The ITS2 region is about 200 nucleotides long, and the nucleotides in the ITS2 sequence can be numbered beginning with the first nucleotide downstream of the 5.8S coding sequence and ending with the last nucleotide directly in advance of the 28S coding sequence. Similar to the entire ITS1-ITS4 amplicon, the ITS2 region can be divided into segments, for example (and without limitation), halves, thirds, quarters, fifths, or tenths.

While the length of the ITS2 sequence is about 200 nucleotides in fungi, the sequence can be shorter or longer in a particular fungal species, thus altering the nucleotide reference numbers for a particular species. For example, an ITS2 sequence from a particular species that is about 180 nucleotides in length could be split in half by nucleotides 1-90 and 91-180, or quarters by nucleotides 1-45, 46-90, 91-135, and 136-180.

Segments of an ITS 1-ITS4 amplicon or an ITS2 region can include one or more nucleotides that overlap into a different a segment (half, quarter, third, tenth, etc.), so long as the majority of the sequence lies within a particular segment. For example, a 25-nucleotide probe or primer corresponding to nucleotides 135 to 160 of a 600 nucleotide ITS1-ITS4 amplicon is considered to fall within the first quarter of the sequence, even though 10 nucleotides overlap into the second quarter.

Nucleic acid molecules can be selected that comprise at least 10, 15, 20, 25, 30, 35, 40, 50, 75, 100, or more consecutive nucleotides of any of these portions of the fungal ITS2 sequence. Furthermore, nucleic acid molecules can include only a portion of a particular probe or primer, such as a sequence of 5, 10, 15, 20, 25, 30, 40, 50, or more contiguous nucleotides of a particular primer, including (without limitation) the probes and primers disclosed herein.

Primers include the universal fungal primers for PCR amplification commonly known as ITS 1, ITS3, ITS4. These primers are listed in Table 1, illustrated in FIG. 2, and their sequences are provided by SEQ ID NOS: 1, 2, and 3.

As one non-limiting example, the Dm probe can comprise at least 25 consecutive nucleotides of the first half (nucleotides 1-100), first third (nucleotides 1-66), first quarter (nucleotides 1-50), second third (nucleotides 67-132), or second quarter (nucleotides 50-100) of an ITS2 region 200 nucleotides in length. Sequences from particular fungi corresponding to Dm are illustrated in FIG. 3. In this figure, the Dm sequence is indicated by the shaded box in the upper portion of FIG. 3A; sequences are compared to that of *Histoplasma capsulatum*, with identical bases indicated by a period (.) and a gap in the sequence indicated by a dash (-). The Dm sequence begins at about nucleotide 30 to about nucleotide 60 of the ITS2 sequence, depending on the species of fungus, for example (and without limitation) at nucleotide 51 in *Histoplasma capsulatum*, nucleotide 45 in *Blastomyces dermatitidis*, nucleotide 51 in *Coccidioides immitis*, nucleotide 45 in *Paracoccidioides brasiliensis*, and nucleotide 44 in *Penicillium marneffei*. The Dm probe includes the particular nucleotide sequence from *Histoplasma capsulatum* and similar sequences, such as sequences demonstrating about 55% to about 100% sequence identity, such as about 55%, 60%, 65%, 70%, 75%, 80%, 85%, 90%, 95%, 96%, 99% or greater sequence identity, including the particular sequences of the fungi illustrated in FIGS. 3A-B.

As another, non-limiting example, the Pm probe—a species-specific probe to *P. marneffei*—can comprise at least 18 consecutive nucleotides of the portion consisting of nucleotides 90-140 of the *P. marneffei* ITS2 sequence. Other species-specific and microbe-specific probes are illustrated by shaded boxes in FIG. 3A-B.

A “species-specific” probe is a probe shown to be capable of differentiating a species of fungus from another species in the same genus. A “microbe-specific” probe is a probe that is capable of differentiating a species of fungus from another species in a different genus, but that has not yet been shown to be capable of differentiating that species of fungus from another species in the same genus. However, if a microbe-specific probe is shown to be capable of differentiating fungi within the same genus, then that probe can properly be described as “species specific.” For example, the Bd probe is considered to be a microbe-specific probe capable of differentiating *B. dermatitidis* from other fungi. Because *B. dermatitidis* is the only currently known species within the *Blastomyces* genus, it cannot currently be determined whether the Bd probe also is a species-specific probe. Another example of a microbe-specific probe would be a probe capable of differentiating *Penicillium* species from *Candida* species, which can be described as a “genus-specific” probe.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences is expressed in terms of the similarity between the sequences, otherwise referred to as sequence identity. Sequence identity is frequently measured in terms of percentage identity, similarity, or homology; a higher percentage identity indicates a higher degree of sequence similarity. Homologs of fungal ITS2 sequences will possess a relatively high degree of sequence identity when aligned. Typically, fungal ITS2 sequences are about 80 to 100% identical at the nucleotide level when comparing homologs of the same species. However, within particular portions of the IFS2 region, the sequence identity can be more or less. For example, among the dimorphic fungi, the portion of the ITS2 region adjacent to the 5.8S coding sequence demonstrates greater sequence identity (such as about 84 to 100%), while the portion of the ITS2 region adjacent the 28S sequence demonstrates lesser sequence identity (such as about 0 to 44%).

The NCBI Basic Local Alignment Search Tool (BLAST) (Altschul et al. (1990) J. Mol. Biol. 215:403-410) is available from several sources, including the National Center for Biotechnology Information (NCBI, Bethesda, Md.) and on the Internet, for use in connection with the sequence analysis programs blastp, blastn, blastx, tblastn and tblastx. It can be accessed through the NCBI website. A description of how to determine sequence identity using this program also is available on the NCBI website.

When less than the entire sequence is being compared for sequence identity, homologs typically possess at least 75% sequence identity over short windows of 10-20 amino acids, and can possess sequence identities of at least 85%, or at least 90%, or even 95% or greater, depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. and P. Tijssen, Hybridization With Nucleic Acid Probes, Part I: Theory and Nucleic Acid Preparation (Laboratory Techniques in Biochemistry and Molecular Biology) (Elsevier Science Ltd., NY, N.Y., 1993). Nucleic acid molecules that hybridize under stringent conditions to a fungal ITS2 sequence will typically hybridize to a probe based on either an entire ITS2 sequence or selected portions of the ITS2 sequence under wash conditions of 2×SSC at 50° C.

For purposes of the present disclosure, “stringent conditions” encompass conditions under which hybridization will only occur if there is less than 25% mismatch between the hybridization molecule and the target sequence. “Stringent conditions” may be broken down into particular levels of stringency for more precise definition. Thus, as used herein, “moderate stringency” conditions are those under which molecules with more than 25% sequence mismatch will not hybridize; conditions of “medium stringency” are those under which molecules with more than 15% mismatch will not hybridize; and conditions of “high stringency” are those under which sequences with more than 10% mismatch will not hybridize. Conditions of “very high stringency” are those under which sequences with more than 6% mismatch will not hybridize.

Transformed: A transformed cell is a cell into which a nucleic acid has been introduced by molecular biology techniques. The term “transformation” encompasses all techniques by which a nucleic acid molecule might be introduced into such a cell, including transfection with viral vectors, transformation with plasmid vectors, and introduction of naked DNA by such techniques as electroporation, lipofection, and particle gun acceleration.

Vector: A nucleic acid molecule as introduced into a host cell, thereby producing a transformed host cell. A vector can include nucleic acid sequences that permit it to replicate in a host cell, such as an origin of replication. A vector also can include one or more selectable marker nucleic acids and other genetic elements.

High Throughput Isolation of Fungal DNA

Disclosed is a high-throughput method for isolating DNA from prokaryotic and eukaryotic cells, including cells of bacteria, fungi, protozoans, animals, and plants. Cells are mechanically disrupted using plural granular materials, such as beads or microspheres, and standard laboratory equipment. For example, the mechanical energy for disrupting cells can be supplied by a rotary incubator (such as models available from New Brunswick Scientific, Edison, N.J.), rather than specialized equipment. After cell disruption, cellular proteins are precipitated, such as by using a concentrated salt solution, and the samples are treated with RNase. The remaining nucleic acids (i.e., DNA) are collected from the sample, such as by spin columns or precipitation by alcohol, followed by centrifugation.

The granular materials can be composed of any substance, such as metal, polymer, or silica, and the individual grains can be of any shape, for example (but not limited to) spherical, cubical, or pyramidal. Some embodiments employ glass microspheres.

The grains can be of any suitable size. In some embodiments, the grains are about 10 µm to 5 mm, such as about 50 µm to 4 mm, or, in particular embodiments, about 100 µm to about 3 mm.

The plural granular materials can be differentiated by type of material or size of grains. In some embodiments, glass microspheres of varying sizes, such as about 100 µm to about 3 mm, are used. In particular embodiments, three different sizes of glass microspheres are used: a first set of glass microspheres of about 100 µm, such as 106 µm; a second set of glass microspheres of about 0.5 mm; and a third set of glass microspheres of about 3 mm. In other particular embodiments, the microspheres can differ in diameter by a particular ratio, such as about 1:2, 1:3, 1:4, 1:5, 1:6, 1:7, 1:8, 1:9, 1:10, 1:15, 1:20, 1:30, 1:50, 1:100, 1:500, or any other ratio within this range. For example, and without limitation, if three differently sized microspheres are used'A, B, and C—the A:B diameter ratio can be about 1:5, the B:C diameter ratio can be about 1:6, and the A:C diameter ratio can be about 1:30. Alternatively, the ratio of diameters can be about X:Y:Z, where X is about 0.05 to 0.2, Y is about 0.3 to 0.7, and Z is about 2.5 to 3.5. In particular embodiments, the ratio is about 0.1 to 0.5 to 3.0.

In still other particular embodiments, the microspheres can be selected according to a desired size difference. For example, and without limitation, a diameter difference of about (or at least about) 100 µm, 200 µm, 500 µm, 1 mm, 2 mm, or 5 mm can be provided.

Multiple biological samples can be processed together via this high-throughput method. Samples can be arranged in an array, such as a multi-well plate. Each well can contain a sample from the same or different source, and plates with different numbers of wells can be used, such as an 18-well, 24-well, 36-well, 48-well, 72-well, 96-well, or 120-well plate. Plates having greater numbers of wells can be used, and the individual wells can be of any suitable volume, such as (and without limitation) about 0.5 ml, 1.0 ml, or 2.0 ml. In particular embodiments, a 96-well plate having 2.0 ml wells is used.

One particular, non-limiting example of this high-throughput method is provided in Example 2.

Probes

Probes capable of hybridizing to isolated fungal rDNA are disclosed, some of which are species-specific or microbe-specific. Additionally, probes that differentiate dimorphic fungi (which, in turn, can be microbe-specific or species-specific from other yeast-like fungi, or yeast species, are disclosed and referred to herein as "dimorphic probes." The species-specific, microbe-specific, and dimorphic probes include sequences obtained from the ITS2 sequence of fungal DNA.

Figure 3A:
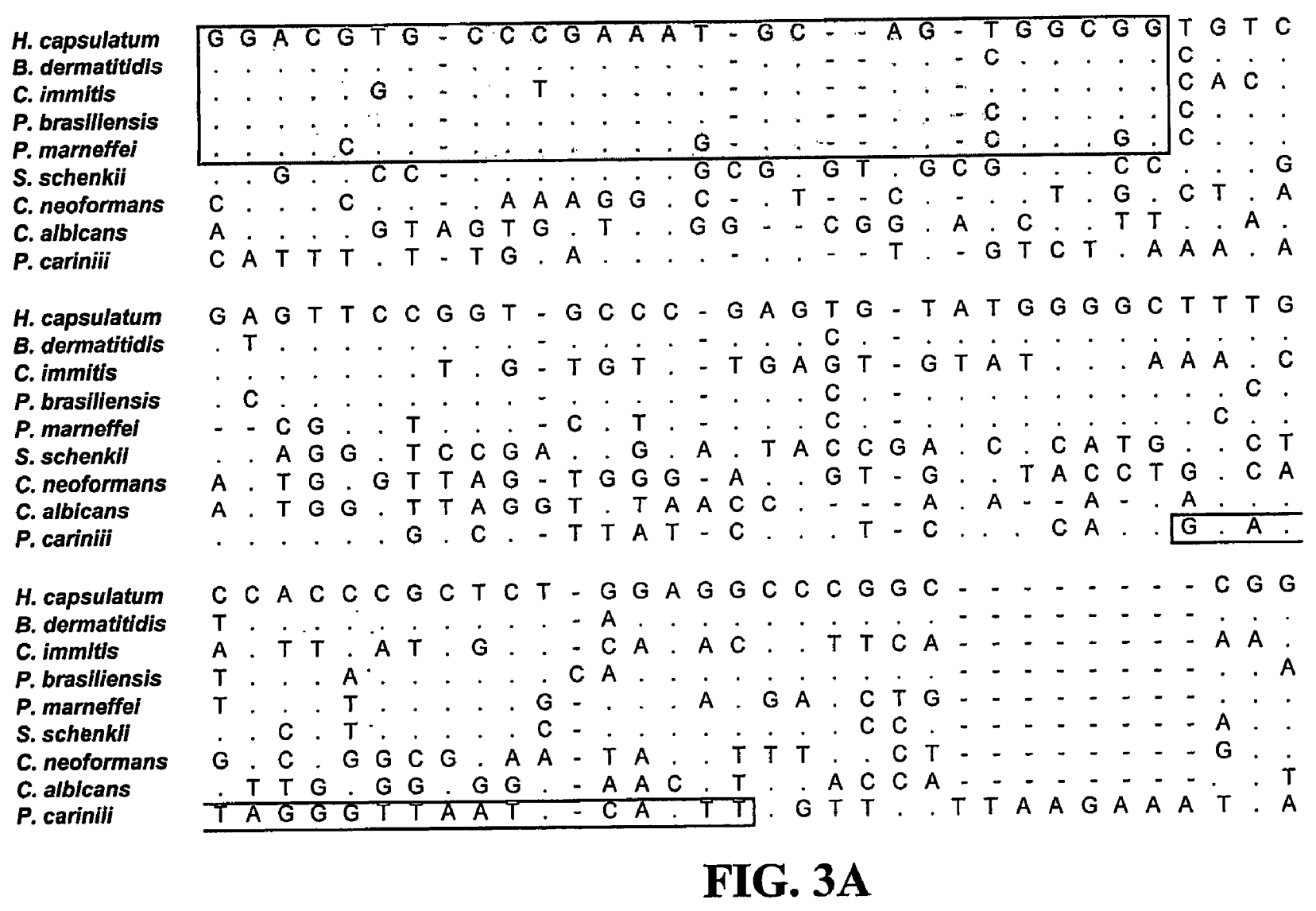

One particular dimorphic probe, Dm, is described in Table 1 and FIG. 3. Other, exemplary, non-limiting, probes include the species-specific and microbe-specific probes listed in Tables 1-3.

In some embodiments, the species-specific probes correspond to sequences in the downstream half, third, quarter, fifth, sixth, or tenth of the ITS2, such as sequences adjacent to the 28S coding sequence, while the dimorphic probes correspond to sequences in the upstream half, third, quarter, fifth, sixth, or tenth of the ITS2, such as sequences adjacent to the 5.8S coding sequence. However, in some embodiments, a minor portion of the probe sequence corresponds to sequences that fall within the 5.8S or 28S coding sequences. Particular dimorphic probes correspond to sequences of about 15 to about 50 nucleotides, such as about 25 nucleotides, within the portion of the ITS2 region from about nucleotide 40 to about nucleotide 80, while particular microbe-specific probes correspond to sequences of about 10 to about 50 nucleotides, such as about 15 to about 30 nucleotides, within the portion of the ITS2 region from about nucleotide 90 to about nucleotide 200.

Detecting Fungal rDNA Sequences

The presence of a fungus within a sample can be detected using the probe and primer sequences described herein. Fungal DNA can be directly detected or amplified prior to detection, and identification of the fungi from which the DNA originated can be confirmed by species-specific, microbe-specific, and/or dimorphic oligonucleotide probes. The methods described herein can be used for any purpose where the detection of fungi is desirable, including diagnostic and prognostic applications, such as in laboratory and clinical settings.

Appropriate samples include any conventional environmental or biological samples, including clinical samples obtained from a human or veterinary subject, for instance blood or blood-fractions (e.g., serum), sputum, saliva, oral washings, skin scrapes, biopsied tissue, BAL, cerebrospinal fluid, or prostate fluid. Standard techniques for acquisition of such samples are available. See, e.g. Schluger et al., J. Exp. Med. 176:1327-33 (1992); Bigby et al., Am. Rev. Respir. Dis. 133:515-18 (1986); Kovacs et al., NEJM 318:589-93 (1988); and Ognibene et al., Am. Rev. Respir. Dis. 129:929-32 (1984). Serum or other blood fractions can be prepared according to standard techniques; about 200 µL of serum is an appropriate amount for the extraction of DNA for use in amplification reactions. See, e.g., Schluger et al.; Ortona et al., Mol. Cell Probes 10:187-90 (1996).

The sample can be used directly or can be processed, such as by adding solvents, preservatives, buffers, or other compounds or substances.

Once a sample has been obtained, DNA can be extracted using standard methods. For instance, rapid DNA preparation can be performed using a commercially available kit (e.g., the InstaGene Matrix, BioRad, Hercules, Calif.; the NucliSens isolation kit, Organon Teknika, Netherlands; the QIAGEN Tissue Kit, QIAGEN, Inc., Valencia, Calif.). The DNA preparation technique can be chosen to yield a nucleotide preparation that is accessible to and amenable to nucleic acid amplification. Particular DNA extraction and preparation methods include (without limitation) the high-throughput method described above and the method described in Example 1 below.

Fungal nucleotide sequences can be detected through the hybridization of an oligonucleotide probe to nucleic acid molecules extracted from a biological or environmental sample, including a clinical sample. The sequence of appropriate oligonucleotide probes will correspond to a region within one or more of the fungal nucleotide sequences disclosed herein. Standard techniques can be used to hybridize fungal oligonucleotide probes to target sequences, such as the techniques described in U.S. Pat. Nos. 5,631,132; 5,426,027; 5,635,353; and 5,645,992; and PCT publication WO 98/50584.

In some embodiments, the probe is detectably labeled in some fashion, either with an isotopic or non-isotopic label; in alternative embodiments, the target (template) nucleic acid is labeled. Non-isotopic labels can, for instance, comprise a fluorescent or luminescent molecule, or an enzyme, co-factor, enzyme substrate, or hapten. The probe is incubated with a single-stranded preparation of DNA, RNA, or a mixture of both, and hybridization determined after separation of double and single-stranded molecules. Alternatively, probes can be incubated with a nucleotide preparation after it has been separated by size and/or charge and immobilized on an appropriate medium.

In some embodiments, target fungal nucleotide sequences in a sample are amplified prior to using a hybridization probe for detection. For instance, it can be advantageous to amplify part or all of the ITS2 sequence, then detect the presence of the amplified sequence pool. Any nucleic acid amplification method can be used, including the polymerase chain reaction (PCR) amplification. In particular embodiments, the PCR-EIA method is used for the amplification and detection of fungi; the PCR-EIA is described herein, such as in Example 8, and illustrated in FIGS. 1-2.

The sequential use of universal fungal primers for PCR amplification and microbe-specific probes can be used to identify fungi. Universal fungal primers directed to the ITS1 and ITS4 regions of rDNA (See FIG. 2) allow amplification of a major portion of rDNA from most fungi, rather than that from only a single fungal species. The rDNA gene offers a suitable amplification target, not only because it contains binding sites for universal fungal primers, but also because the chromosome on which this gene is located contains approximately 100 gene copies that offer "pre-amplification" to increase amplicon yield and test sensitivity. Therefore, in some embodiments, the use of universal primers and a multiple copy gene target (rDNA) has greater utility and sensitivity for the identification of fungi in diverse samples than offered by gene targets of other embodiments.

While PCR-EIA offers one method of amplicon detection and identification of fungi, other methods of identification can be used. Amplicons can be produced using microbe-specific primers and detected by electrophoresis in agarose gels and ethidium bromide staining. See, e.g., Aoki, F. H., et al., J. Clin. Microbiol. 37:315-20 (1999). The presence of a band in such an agarose gel is considered a positive result using specific primers. However, because different species of fungi can produce similar size amplicons, amplicon size detection can be supplemented with other identification methods.

Alternatively, the presence of a unique banding pattern after restriction enzyme digestion of fungal DNA, including DNA obtained by amplification, such as PCR, can be used for species identification, including methods commonly known as "genetic fingerprinting" based on restriction-fragment length polymorphism (RFLP) or randomly amplified polymorphic DNA (RAPD) analysis. See, e.g., Morace, G., M. et al., J. Clin. Microbiol. 35:667-72 (1997).

Species-specific probes can be used to obtain a final identification of a fingus using Southern blot, slot blot, dot blot, or another similar method. See, e.g., Sandhu, G. S., et al., J. Clin. Microbiol. 35:1894-96 (1997); Sandhu, G. S., et al., J. Clin. Microbiol. 33:2913-19 (1995); and Tanaka, K., et al., J. Clin. Microbiol. 34:2826-28 (1996). Additionally, an identification method using universal primers was developed by Turenne et al. (J. Clin. Microbiol. 37:1846-51 (1999)), in which fungi are identified by the exact size of amplified DNA using an automated fluorescent capillary electrophoresis system.

The probes described herein not only provide a means to identify fungi in culture, but also aid in the histological identification of fungi in other samples, such as environmental and biological samples. Application of these probes to fungi in tissue sections can allow the differentiation of truly invasive organisms from simple colonizers, and multiple techniques can be employed to identify fungi in tissue using these probes. In some embodiments, fungal DNA is extracted from the tissue and identified by PCR-EIA. In other embodiments, the probes can be used for in situ hybridization, allowing localization of fungal DNA directly in the tissue. In still other embodiments, the combination of PCR and in situ hybridization procedures, where the target DNA is both amplified and hybridized in situ, can be employed. None of these methods should be considered mutually exclusive, however.

PCR-EIA allows amplification and detection of small quantities of DNA, such as quantities of only a few nanograms, a few picograms, or less. Conceivably, PCR-EIA can be able to detect only a few molecules of fungal DNA present in a sample. However, sensitivity of a PCR-based assay, such as PCR-EIA, can be enhanced by various modifications of the technique. For example, nested PCR utilizes a second set of primers, internal to the original set of primers, to re-amplify the target DNA using the amplicons from the first PCR as a template for the second PCR. See, e.g., Podzorski, R. P., and D. H. Persing, in Manual of Clinical Microbiology, 6th ed., P. R. Murray, et al. (eds.), (ASM Press, Washington, DC, 1995); and Rappelli, P., R., et al., J. Clin. Microbiol. 36:3438-40 (1998). Additionally, the PCR reaction can be continued through more cycles, continuing the geometric increase of DNA amplified, and alternative forms of Taq polymerase are available that have increased stability and accuracy throughout an increased number of PCR cycles. Commercially available Taq polymerases can be obtained from Roche Molecular Systems (Pleasanton, Calif.), Seikagaku America (Falmouth, Conn.), and other commercial suppliers.

Fungal Profiling Arrays

An array containing a plurality of heterogeneous, dimorphic, microbe-specific, and/or species-specific probes can be used to screen a sample for the presence of a fungus. Such arrays can be used to rapidly detect and identify a fungus, for example a dimorphic fungus or a fungus of a particular species or genus, such as *Penicillium marneffei*.

Arrays are arrangements of addressable locations on a substrate, with each address containing a nucleic acid, such as a probe. In some embodiments, each address corresponds to a single type or class of nucleic acid, such as a single probe, though a particular nucleic acid can be redundantly contained at multiple addresses. A "microarray" is a miniaturized array requiring microscopic or otherwise assisted examination for detection of hybridization. Larger "macroarrays" allow each address to be recognizable by the naked human eye and, in some embodiments, a hybridization signal is detectable without additional magnification. The addresses can be labeled, keyed to a separate guide, or otherwise identified by location.

In some embodiments, a fungal profile array is a collection of separate probes at the array addresses. As one, non-limiting example, the array can contain the probes listed in Table 1. The fungal profiling array is then contacted with a sample suspected of containing fungal nucleic acids under conditions allowing hybridization between the probe and nucleic acids in the sample to occur. Any sample potentially containing, or even suspected of containing, fungal nucleic acids can be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the fungal DNA or RNA contained within the sample. In alternative embodiments, the array contains fungal DNA or RNA and the array is contacted with a sample containing a probe. In any such embodiment, either the probe or the fungal DNA or RNA can be labeled to facilitate detection of hybridization.

The nucleic acids can be added to an array substrate in dry or liquid form. Other compounds or substances can be added to the array as well, such as buffers, stabilizers, reagents for detecting hybridization signal, emulsifying agents, or preservatives.

Within an array, each arrayed nucleic acid is addressable—its location can be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (e.g., in radially distributed lines, a "spokes and wheel" pattern, or ordered clusters).

An address within the array can be of any suitable shape and size. In some embodiments, the nucleic acids are suspended in a liquid medium and contained within square or rectangular wells on the array substrate. However, the nucleic acids can be contained in regions that are essentially triangular, oval, circular, or irregular. The overall shape of the array itself also can vary, though in some embodiments it is substantially flat and rectangular or square in shape.

Fungal profiling arrays can vary in structure, composition, and intended functionality, and can be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification can be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (e.g., glass or a supported membrane) or flexible (such as a polymer membrane). One commercially available product line suitable for probe arrays described herein is the Microlite line of Microtiter® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses should be distinguishable from signals of neighboring addresses, either by the naked eye (macroarrays) or by scanning or reading by a piece of equipment or with the assistance of a microscope (microarrays).

Addresses in a macroarray can be of a relatively large size, such as large enough to permit detection of a hybridization signal without the assistance of a microscope or other equipment. Thus, addresses of a macroarray can be as small as about 0.1 mm across, with a separation of about the same distance. Alternatively, addresses can be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (i.e., larger addresses will usually be found on larger arrays, while smaller addresses can be found on smaller arrays). Such a correlation is not necessary, however.

The arrays herein can be described by their densities—the number of addresses in a certain specified surface area. For macroarrays, array density can be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GeneChip® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques, similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample can be labeled, such as with a fluorescent label and, after hybridization, the hybridization signals can be detected and analyzed.

Detecting Infection and Disease

The method also includes diagnosing or detecting certain classes of infections with dimorphic fungi, by using the Dm probe (or a fragment or variant thereof) to detect the presence of infection with a dimorphic fungus, such as *H. capsulatum, B. dermatitidis, C. immitis, P. brasiliensis,* or *P. marneffei*. Once the presence of the dimorphic fungal infection is established using the Dm probe, these different dimorphic fungal infections can be further distinguished from one another by exposing the specimen to a microbe-specific or species-specific probe, such as the Hc probe (or a fragment or variant thereof) which specifically binds to *H. capsulatum* but not *B. dermatitidis, C. immitis, P. brasiliensis,* or *P. marneffei*; the Bd probe which binds specifically to *B. dermatitidis* but not *H. capsulatum, C. immitis, P. brasiliensis,* or *P. marneffei*; the Ci probe (or a variant or fragment thereof) which binds specifically to *C. immitis* but not *H. capsulatum, B. dermatitidis, P. brasiliensis,* or *P. marneffei*; the Pb probe (or a variant or fragment thereof) which binds specifically to *H. capsulatum, B. dermatitidis, C. immitis,* or *P. marneffei*; and/or the Pm probe (or a variant or fragment thereof) which binds specifically to *P. marneffei* but not *H. capsulatum, B. dermatitidis, C. immitis,* or *P. brasiliensis*.

As used herein, each species-specific or microbe-specific probe refers to a probe that binds to the nucleic acid sequence of a species with a specificity sufficient to distinguish different species from one another. In particular examples, that specificity is at least 3.0, or at least 7.0, as measured by an EIA index (EI) equal to the optical density of the test DNA (i.e., the probe tested) divided by the optical density of a water blank. One particular, non-limiting example of determining EI is provided in Example 10.

In certain examples, a probe can bind to two species detectably (as with Bd which binds to *B. dermatitidis* with a higher specificity (11.9) than it binds to *C. immitis* (4.3)), but the higher specificity can be used to distinguish the two. Alternatively, a specimen with nucleic acid that detectably binds to the Bd probe also can be probed with the Ci probe, to distinguish *B. dermatitidis* from *C. immitis* infection.

When referring to species-specific or microbe-specific probes, it is understood that this refers to a probe having a specificity of probe binding of at least 3.0 EI for the nucleic acid of the fungus of interest, such as *H. capsulatum, B. dermatitidis, C immitis, P. brasiliensis,* or *P. marneffei.* Particular, non-limiting, examples of the microbe-specific probes are Hc, Ci, or Pb, while Pm is a particular, non-limiting, example of a species-specific probe. However, species-specific and microbe-specific probes also refer to variants, fragments, and longer probes that contain the species-specific or microbe-specific sequences of the disclosed sequences.

A probe specific for a dimorphic fungus refers to a probe having a sequence that binds to the nucleic acid of a dimorphic fungus with sufficient specificity to distinguish the fungus from a non-dimorphic fungus, such as *S. schenckii, C. neoformans,* or other organism, such as *P. carinii.* In particular examples, the probe specifically binds to the dimorphic fungus with a specificity of at least 2.5, 3.0, or 5.0 EI.

A "variant" of a probe includes sequences that have altered nucleic acid sequences, but retain their ability to bind to the target sequences (and identify the fungal target) with sufficient specificity. In some particular examples, no more than 1, 2, 5, or 10 nucleic acids are changed, or the probe retains at least 80%, 85%, 90%, or 95% sequence identity to the original probe. Variants also include probe sequences to which an additional nucleic acid sequence has been added, while still retaining the noted specificity of the probes. Fragments include shortened probe sequences (or subsequences) of a probe that also retains the noted specificity.

Any of these variants or fragments can be screened for retention of specificity by determining the EI of the variant or fragment, such as (and without limitation) by the assay described in Example 10. However, because the EI is based on a ratio, and not an absolute measurement, other techniques for measuring hybridization, rather than optical density of a colored dye, can be used.

Kits

The oligonucleotide primers and probes disclosed herein can be supplied in the form of a kit for use in detection of fungi, including kits for any of the arrays described above. In such a kit, an appropriate amount of one or more of the oligonucleotide primers and/or probes is provided in one or more containers or held on a substrate. An oligonucleotide primer or probe can be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampules, or bottles. In some applications, pairs of primers can be provided in pre-measured single use amounts in individual, typically disposable, tubes or equivalent containers. With such an arrangement, the sample to be tested for the presence of fungal nucleic acids can be added to the individual tubes and amplification carried out directly.

The amount of each oligonucleotide primer supplied in the kit can be any appropriate amount, and can depend on the target market to which the product is directed. For instance, if the kit is adapted for research or clinical use, the amount of each oligonucleotide primer provided would likely be an amount sufficient to prime several PCR amplification reactions. General guidelines for determining appropriate amounts can be found in Innis et al., Sambrook et al., and Ausubel et al. A kit can include more than two primers in order to facilitate the PCR amplification of a larger number of fungal nucleotide sequences.

In some embodiments, kits also can include the reagents necessary to carry out PCR amplification reactions, including DNA sample preparation reagents, appropriate buffers (e.g., polymerase buffer), salts (e.g., magnesium chloride), and deoxyribonucleotides (dNTPs).

Kits can include either labeled or unlabeled oligonucleotide probes for use in detection of fungal nucleotide sequences. The appropriate sequences for such a probe will be any sequence that falls between the annealing sites of the two provided oligonucleotide primers, such that the sequence that the probe is complementary to is amplified during the PCR reaction. In some embodiments, the probe is complementary to a sequence within the fungal ITS2 region.

One or more control sequences for use in the PCR reactions also can be supplied in the kit. Appropriate positive control sequences can be essentially as those discussed above.

Particular embodiments include a kit for detecting and identifying a fungus based on the arrays described above. Such a kit includes at least two different probes (as described above) and instructions. A kit can contain more than two different probes, such as at least 10, at least 25, at least 50, at least 100, or more probes. The instructions can include directions for obtaining a sample, processing the sample, preparing the probes, and/or contacting each probe with an aliquot of the sample. In certain embodiments, the kit includes a device or apparatus for separating the different probes, such as individual containers (e.g., microtubules) or an array substrate (e.g., a 96-well or 384-well microtiter plate). In particular embodiments, the kit includes prepackaged probes, such as probes suspended in suitable medium in individual containers (e.g., individually sealed Eppendorf® tubes) or the wells of an array substrate (e.g., a 96-well microtiter plate sealed with a protective plastic film). In other particular embodiments, the kit includes equipment, reagents, and instructions for extracting and/or purifying nucleotides from a sample.

EXAMPLES

The following examples are provided to illustrate particular features of certain embodiments, but the scope of the claims should not be limited to those features exemplified.

Example 1

Isolation of Fungal DNA

One loopful of yeast phase *B. dermatitidis* (strains 4478, KL-1 (ATCC 26198), or A2 (ATCC 60916)), was inoculated into 10 ml of Brain Heart Infusion broth (Difco, Becton Dickinson, Sparks, Md.) in a 50 µl Erlenmeyer flask and incubated at 37° C. on a rotary shaker (140 rpm) for 48 to 72 h. The suspension was then transferred to a 30 ml centrifuge tube (Oak Ridge, Nalge, Rochester, N.Y.) and centrifuged for 3 min at 2000×g. Genomic DNA was extracted and purified using a commercial kit (PureGene Yeast and Gram Positive DNA Isolation Kit; Gentra Systems Inc., Minneapolis, Minn.) following the manufacturer's protocol.

Mold phase cultures of *Sporothrix schenckii* (ATCC 58251) and *Penicillium marneffei* (strains ATCC 64101, ATCC 58950, and JH05 (gift of Dr. William Merz, Johns Hopkins Medical School, Baltimore, Md.)) were grown in 50 ml of Sabouraud dextrose broth (Difco) in 250 ml Erlenmeyer flasks and incubated at 25° C. on a rotary shaker for 5 days. Growth was harvested by vacuum filtration through sterile filter paper, and the cellular mat was washed three times with sterile distilled $H_2O$ by filtration. The cellular mat was then removed from the filter and placed into a sterile Petri plate, which was then sealed around the edges with Parafilm® (American Can, Neenah, Wis.) and frozen at −20° C. until used.

DNA was extracted by grinding the cellular mats with a mortar and pestle in the presence of liquid nitrogen. Just before use, a portion of the frozen cellular mat, approximately an inch in diameter, was removed from the Petri plate with sterile forceps and placed into an ice-cold, sterile mortar (6 inches diameter). Liquid nitrogen was added to cover the mat and was added as needed to keep the mat frozen during grinding. The fungal mat was ground into a fine powder with a sterile pestle. Fungal DNA was then extracted and purified using serial proteinase K and RNase treatments followed by phenol extraction and ethanol precipitation by standard methods. See Maniatis, et al., Molecular Cloning: A Laboratory Manual (Cold Spring Harbor Laboratory Press, Cold Spring Harbor, N.Y., 1982).

Other DNA was kindly provided as a gift from the following persons: *Histoplasma capsulatum* (strains G186B (ATCC26030), Downs, FLs-1, and B295 (var. *duboisii*)), Dr. Brent Lasker, Centers for Disease Control and Prevention (CDC), Atlanta, Ga.; Coccidioides immitis (strains C635 and C735), Dr. Garry Cole, Medical College of Ohio, Toledo, Ohio; *Paracoccidioides brasiliensis* (strains 265, Pb18, rh, soil (soil isolate from Venezuela)), Dr. Maria Jose Soares Mendes Giannini, Faculdade de Ciencias Farmaceuticas, UNESP, Araraquara, Brazil and Dr. Juan McEwen; Corporacion Para Investigaciones Biologicas, Medellin, Colombia; *C. neoformans* (strains 9759-MU-1 (serotype A), BIH409 (serotype B), K24066TAN (serotype C) and 9375 (serotype D)) and all *Candida* species DNA (*Candida albicans* (strain B311), *Candida glabrata* (CDC Y-65) *Candida krusei* (CDC 259-75), *Candida tropicalis* (CDC 38), and *Candida parapsilosis* (ATCC 22019)), Ms. Cheryl Elie, CDC; and *Pneumocystis carinii* (rat isolate), Dr. Charles Beard, CDC.

Example 2

High-Throughput Preparation of Fungal DNA

Fungi

*Aspergillus fumigatus* (ATCC 42202); *Candida albicans* (CBS-2730); *Fusarium solani* (ATCC 52628); *Mucor racemosus* (ATCC 22365); *Pseudallescheria boydii* (ATCC 36282); *Sporothrix schenckii* (ATCC 28184). *Candida albicans* was cultured on Sabouraud dextrose agar at 37° C., *Sporothrix schenckii* was cultured on potato dextrose agar at 27° C., and the remaining four species were cultured on potato dextrose agar at 37° C.

High-Throughput DNA Extraction

Three types of acid-washed glass beads were added to each well of a sterile 96 deep-well plate capable of holding 2 ml of sample per well (Bellco Glass, Inc., Vineland, N.J.). The amounts and types of glass beads used were: (1) 100 μl of 106 μm glass beads (Sigma Chemical Co., St Louis, Mo.); (2) 100 μl of 3 mm glass beads (Corning, Inc., Corning, N.Y.); and (3) 150 μl of 0.5 mm glass beads (BioSpec Products, Inc., Bartlesville, Okla.). Cells or conidia ($10^8$) of the fungi listed above, suspended in 400 μl of TSTE buffer, were then added to each well. The plate was sealed with a cap mat and shaken for 30 min at 500 rpm in a rotary incubator (New Brunswick Scientific, Edison, N.J.) fitted with a stainless steel utility tray to hold the plate.

DNA Purification

Extracted DNA from each well was purified by first diluting the solution from the well in 300 μl of 6 M NaCl in a 2 ml centrifuge tube and vortexing for 30 seconds. Each tube was centrifuged at 2750×g for 30 minutes, and about 700 μl of the supernatant was transferred to a fresh 1.5 ml Eppendorf® tube where it was washed by centrifugation with 700 μl of isopropanol. The supernatant was removed and 300 μl of 70% ethanol was added to the tube. The sample was again centrifuged at 10,000×g for 30 minutes, the supernatant removed, and the pellet was air dried for 30 min. After air-drying, 50 μl TE and 1 μl of 500 μg/ml of RNase was added. The sample was then incubated at 37° C. for 30 min. The DNA was then resuspended in 50 μl TE buffer.

DNA Quantitation

The quantity of DNA isolated in each sample was estimated using the $A_{260/280nm}$ ratio. Absorbance measurements were accomplished using a Hoefer DyNA™ 200 fluorometer with 2 μl of Hoescht 333258 dye diluted for low-range DNA detection (Amersham Pharmacia Biotech, Inc., Piscataway, N.J.) added to each 2 μl of sample.

PCR Amplification

The ITS3 and ITS4 universal fungal primers were used to amplify a region of the fungal rRNA gene (see FIG. 1). The reaction mixture contained 5 μl of 10× PCR buffer; 1 μl of dNTPs (0.2 μM); 0.5 μl of each primer (20 μM); 2.5 U of Taq DNA polymerase (Roche); and 2 μl of template DNA (5 ng). Samples were placed in a Perkin-Elmer 9600 thermal cycler at 95° C. for 30 minutes to denature DNA and then for 36 cycles of 95° C. for 30 seconds (denaturation); 58° C. for 30 seconds (annealing); 72° C. for 1 minute (extension); and a final extension step of 72° C. for 10 minutes were conducted.

Example 3

Comparison of High-Throughput Preparation of Fungal DNA with Standard Methods

The high-throughput technique described in Example 2 was compared with other standard DNA extraction techniques.

DNA Extraction by Enzymatic Digestion

Enzymatic digestion with lyticase was performed by gentle vortex mixing after suspending $10^8$ cells or conidia in 500 μl of lysis buffer A (IM sorbitol, 0.05 M sodium phosphate (monobasic), 0.1% 2-mercaptoethanol, 100 μg/ml lyticase (Sigma Chemical Co.)). Cell suspensions were then incubated in a stationary mode for 3 h at 37° C. Nuclei were lysed by the addition of 100 μl of lysis buffer B (10% SDS and 0.05 M EDTA (pH 8.0) (Sigma Chemical Co.)).

DNA Extraction by Glass Bead Beater

Cells or conidia ($10^8$) were suspended in 400 μl of TSTE buffer (5% Triton X-100, 100 mM NaCl, 10 mM Tris (pH 8.0), 1 mM EDTA) and transferred to a 2 ml tube containing 400 μl of glass beads (Q-BIOgene, Carlsbad, Calif.). TSTE buffer (400 μl; see above) was added and the tube was placed in a FastPrep® instrument (Q-BIOgene). The sample was processed for 45 seconds on the highest setting and then cooled on ice for 5 minutes.

DNA Extraction by Liquid Nitrogen Grinding

This method was carried out under a fume hood. Cells or conidia ($10^8$) were transferred into a pre-cooled, sterile mortar using a sterile inoculating loop. Five ml of liquid nitrogen was added, cells were frozen and manually ground into a fine powder using a sterile pestle. One ml of TSTE buffer (see above) was added, and the mortar and pestle were allowed to soak in the buffer for 30 minutes before transfer of the liquid to a 2 ml centrifuge tube.

Comparison Results

DNA was purified and amplified by PCR substantially as described in Example 2, except that the initial centrifugation step of DNA purification was carried out at 10,000×g for 30 minutes, rather than 2750×g for 30 minutes as used in the high-throughput method.

Figure 4:
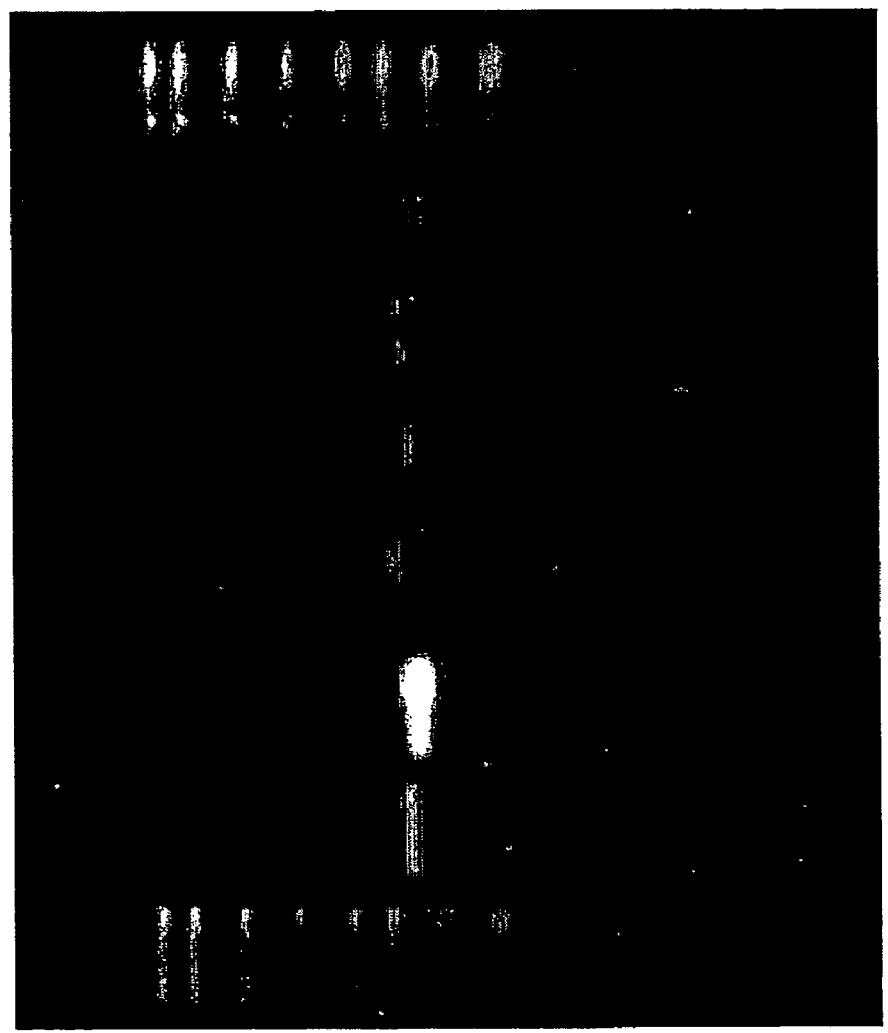
FIG. 4 is a digital image of PCR products amplified from DNA extracted from fungi using the disclosed high-throughput method and separated by size on an agarose gel.
Figure 5:
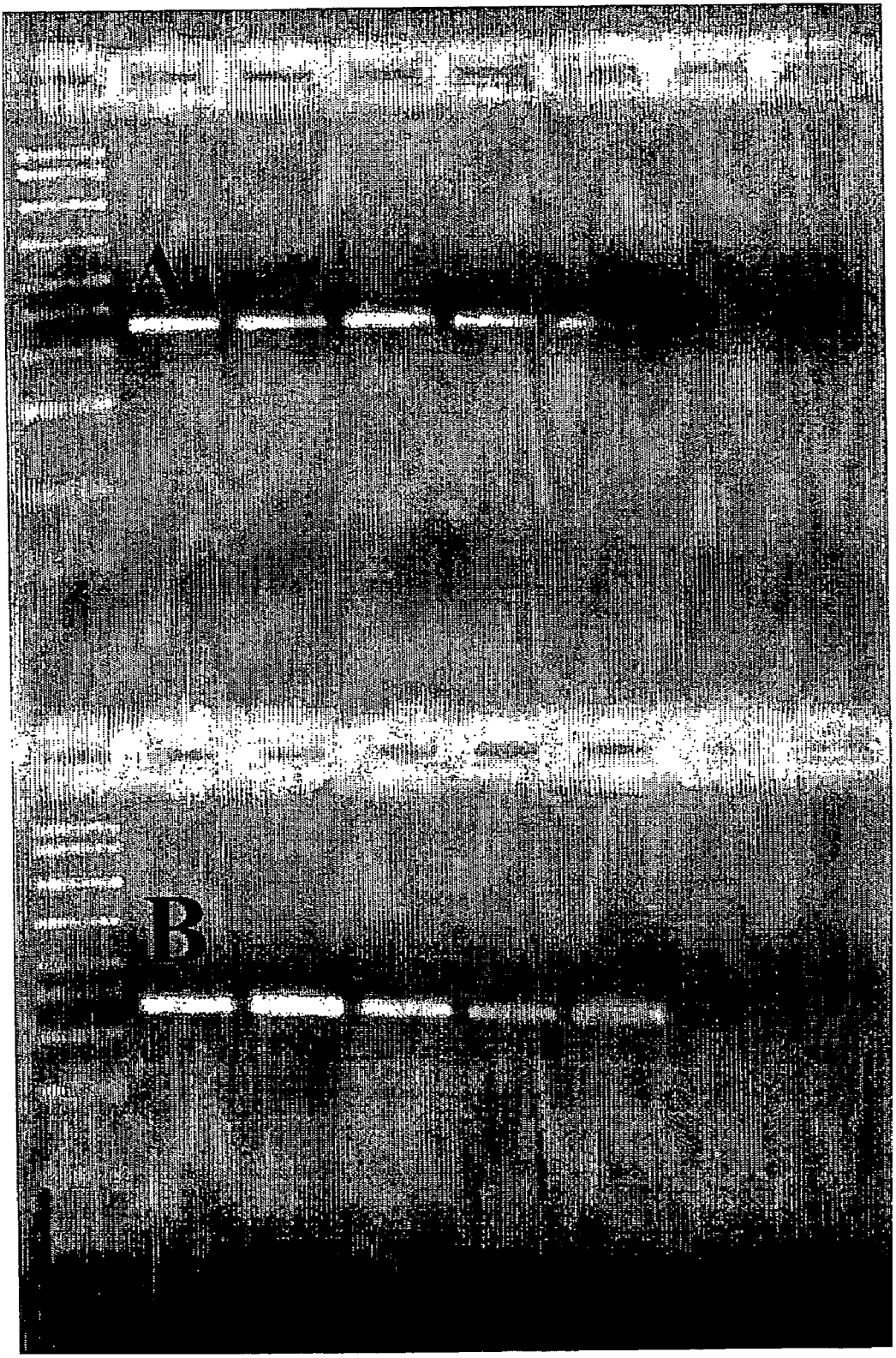
FIG. 5 is a digital image of an agarose gel demonstrating PCR sensitivity based on fungal genomic DNA isolated by the disclosed high throughput method.

DNA extraction by the high-throughput method described in Example 2 was unexpectedly superior to the other three methods—enzymatic digestion, glass bead beater, and liquid nitrogen grinding. The high-throughput method required minimal production time (less than 2 hours, compared to up to 4 hours for the other DNA extraction methods), needed no specialized equipment (unlike the glass bead beater method, which requires a FastPrep instrument), and up to 96 samples could be processed at once (compared to only a single sample or a few samples for the enzymatic digestion and liquid nitrogen grinding method, and up to 12 samples for the glass bead beater method). Furthermore, the high-throughput method produced a DNA yield suitable for typing purposes (30±2 ng/μl, n=6) and no expensive enzymes were needed (compared to the enzymatic degradation method). FIG. 4 is a digital print of an agarose gel showing PCR products after DNA isolation using the high-throughput method. Lane M is a 100-bp DNA ladder (1000 to 100 bp), while lanes 1 to 6 are amplicons from *F. solani, M. racemosus, S. schenckii, A. fumigatus, P. boydii,* and *C. albicans,* respectively. FIG. 5 is a digital print of an agarose gel demonstrating PCR sensitivity based on (A) *A. fumigatus* (B) *C. albicans* genomic DNA isolated by the high-throughput method. Lanes 1 to 6, 100 pg, 10 pg, 1 pg, 100 fg, 10 fg, and 1 fg of DNA, respectively, after PCR amplification. Lane 7, water control. Lane M, 100-bp DNA ladder (1000 to 100 bp).

Example 4

Preparation of Primers and Probes

All primers and probes were synthesized by β-cyanoethyl phosphoramidite chemistry using a 394 or expedite automated DNA synthesizer (PE Applied Biosystems, Foster City, Calif.). ITS3, a universal fungal sequence located in the 5.8S region of the rRNA gene and contained within the region amplified by ITS1 and ITS4 primers (see Lott, et al., *Yeast* 9:1199-206 (1993); and White, T. J., et al., in M. A. Innis, et al. (ed.), PCR Protocols: A guide to methods and applications (Academic Press, San Diego, Calif., 1990) was biotinylated at the 5' end by incorporating dimethyoxytrityl-biotin-carbon-6-phosphoramidite during its synthesis. This biotinylated probe (ITS3-B) was then purified by reverse phase liquid chromatography. Digoxigenin-labeled probes were synthesized with a 5'-terminal amine group using 5' Amino-Modifier C6 (Glen Research, Sterling, Va.), mixed with a 10-fold molar excess of digoxigenin-3-O-methylcarbonyl-ε-aminocaproic acid N-hydroxysuccinimide ester (Roche Molecular Biochemicals, Indianapolis, Ind.) in 0.1 M sodium carbonate buffer, pH 9.0, and incubated at ambient temperature overnight. The digoxigenin-labeled probes were then purified by reverse-phase high pressure liquid chromatography. See Becker, et al., J. Chromatogr. 326:293-299 (1985).

Sequences and locations in the rRNA gene of these primers and probes are depicted in Table 1 and FIG. 1, respectively. All primers and probes were synthesized by the CDC Biotechnology Core Facility.

Example 5

Microbe-Specific Probes

DNA sequences of the ITS2 region of the fungal rRNA gene (see FIG. 1) were obtained from GenBank and are listed in Table 1.

TABLE 1

Sequences of oligonucleotide primers and probes.

| | SEQUENCE (5' to 3') | SEQ ID NO: | OLIGONUCLEOTIDE LABELING |
|---|---|---|---|
| PCR PRIMERS | | | |
| ITS1 | TCCGTAGGTGAACCTGCGG | 1 | Universal forward primer |
| ITS4 | TCCTCCGCTTATTGATATGC | 2 | Universal reverse primer |
| PROBES | | | |
| ITS3-B | GCATCGATGAAGAACGCAGC | 3 | 5'-biotin-labeled universal capture probe |
| Dm | GGACGTGCCCGAAATGCAGTGGCGG | 4 | 5'-digoxigenin-labeled probe for all endemic dimorphic fungi |
| Hc | ACCATCTCAACCTCCTTTTTCACACCAGG | 5 | 5'-digoxigenin-labeled probe for *Histoplasma capsulatum* |
| Bd | GGTCTTCGGGCCGGTCTCCCC | 6 | 5'-digoxigenin-labeled probe for *Blastomyces dermatitidis* |
| Ci | CTCTTTTTTTTATTATATCC | 7 | 5'-digoxigenin-labeled probe for *Coccidioides immitis* |

TABLE 1-continued

Sequences of oligonucleotide primers and probes.

| | SEQUENCE (5' to 3') | SEQ ID NO: | OLIGONUCLEOTIDE LABELING |
|---|---|---|---|
| Pb | CACTCATGGACCCCGG | 8 | 5'-digoxigenin-labeled probe for *Paracoccidioides brasiliensis* |
| Ss | GACGCGCAGCTCTTTTTA | 9 | 5'-digoxigenin-labeled probe for *Sporothrix schenckii* |
| Pm | GGGTTGGTCACCACCATA | 10 | 5'-digoxigenin-labeled probe for *Penicillium marneffei* |
| Cn | CCTATGGGGTAGTCTTCGG | 11 | 5'-digoxigenin-labeled probe for *Cryptococcus neoformans* |
| Pc | GTAGTAGGGTTAATTCAATT | 12 | 5'-digoxigenin-labeled probe for *Pneumocystis carinii* |

Those fungi that did not have sequences available in GenBank (*P. brasiliensis, S. schenckii* and *P. marneffei*) were sequenced using a dye terminator cycle sequencing kit (ABI PRISM, Applied Biosystems, Perkin Elmer, Foster City, Calif.) and sequences have since been deposited with GenBank by our laboratory or by others (Accession numbers: *Sporothrix schenckii*, AF117945; *P. brasilieisis*, AF322389; *P. marneffei*, L37406). Briefly, primary DNA amplifications were conducted using ITS1 and ITS4 as primers. The DNA was purified using QIAquick Spin Columns (Qiagen Corp., Chatsworth, Calif.) and eluted with 50 ml of heat-sterilized Tris-EDTA buffer (10 mM Tris, 1 mM EDTA, pH 8.0). Sequencing was performed in both the forward and the reverse directions. The PCR reaction mix (20 µl) containing 9.5 µl terminator premix, 2 µl (1 ng) DNA template, 1 µl primer (either a forward or reverse primer, 3.2 pmol), and 7.5 µl heat-sterilized distilled $H_2O$ was placed into a pre-heated (96° C.) Perkin-Elmer 9600 thermal cycler for 25 cycles of 96° C. for 10 sec, 50° C. for 5 sec, and 60° C. for 4 min. The PCR product was then purified before sequencing using CentriSep spin columns (Princeton Separations, Inc., Adelphia, N.J.). DNA was then vacuum dried, resuspended in 6 µl of formamide-EDTA (5 µl deionized formamide plus 1 µl of 50 mM EDTA, pH 8.0), and denatured for 2 min at 90° C. before subjection to sequencing using an automated capillary DNA sequencer (ABI Systems, Model 373, Bethesda, Md.).

Sequences were aligned, and a comparison was performed to determine unique sequences that could be used for the development of specific digoxigenin-labeled oligonucleotide probes. The initial screen for specificity of the probe sequences was performed using BLAST software (GCG, Madison, Wis.). Probe sequences determined to be unique were then synthesized and digoxigenin-labeled as described above.

Example 6

PCR Amplification using ITS1 and ITS4 as Primers

The PCR reaction mix consisted of 10 mM Tris-HCl buffer containing 50 mM KCl, pH 8.0 (Roche), 1.5 mM $MgCl_2$ (Roche), 0.2 mM dNTP (TaKaRa Shuzo Co. Ltd; Otsu, Shiga, Japan) and 1.25 U Taq polymerase (TaKaRa Shuzo). Primers ITS1 and ITS4 were added to a final concentration of 0.2 mM each. Template DNA was added at a final concentration of 1 ng per 50 µl reaction mix. For each experiment, at least one reaction tube received water in place of template DNA as a negative control. Amplification was performed in a Model 9600 thermocycler (Perkin Elmer, Emeryville Calif.). Initial denaturation of template DNA was achieved by heating at 95° C. for 5 minutes. This was followed by 30 cycles of 30 s at 95° C., 30 s at 58° C., and 1 min at 72° C. A final extension step was conducted for 10 min at 72° C. Appropriate controls were included and PCR contamination precautions were followed. Fujita, S., et al., J. Clin. Microbiol. 33:962-67 (1995); Kwok, S., and R. Higuchi, Nature 339:237-38 (1989).

Example 7

Confirming PCR Amplification by Agarose Gel Electrophoresis

To verify that the specific DNA target was appropriately amplified and was of the expected size, the PCR amplicons were subjected to agarose gel electrophoresis and bands were visualized after ethidium bromide staining.

Gels consisted of 1% agarose LE (Boehringer Mannheim, Indianapolis, Ind.) and 1% NuSieve GTG agarose (FMC Bioproducts, Rockland, Me.) or 2% Metaphore agar (FMC Bioproducts) dissolved in TBE buffer (0.1 M Tris, 0.09 M boric acid, 0.001 M EDTA, pH 8.4). Five microliters of the PCR amplicons were combined with 1 µl of tracking dye (Roche) and then added to each well of the agarose gel. Electrophoresis was conducted at 70-80 V for 45-60 minutes. The gel was stained with ethidium bromide for 30 min and washed in deionized water for 30 min before examination on a UV transilluminator.

Figure 7:
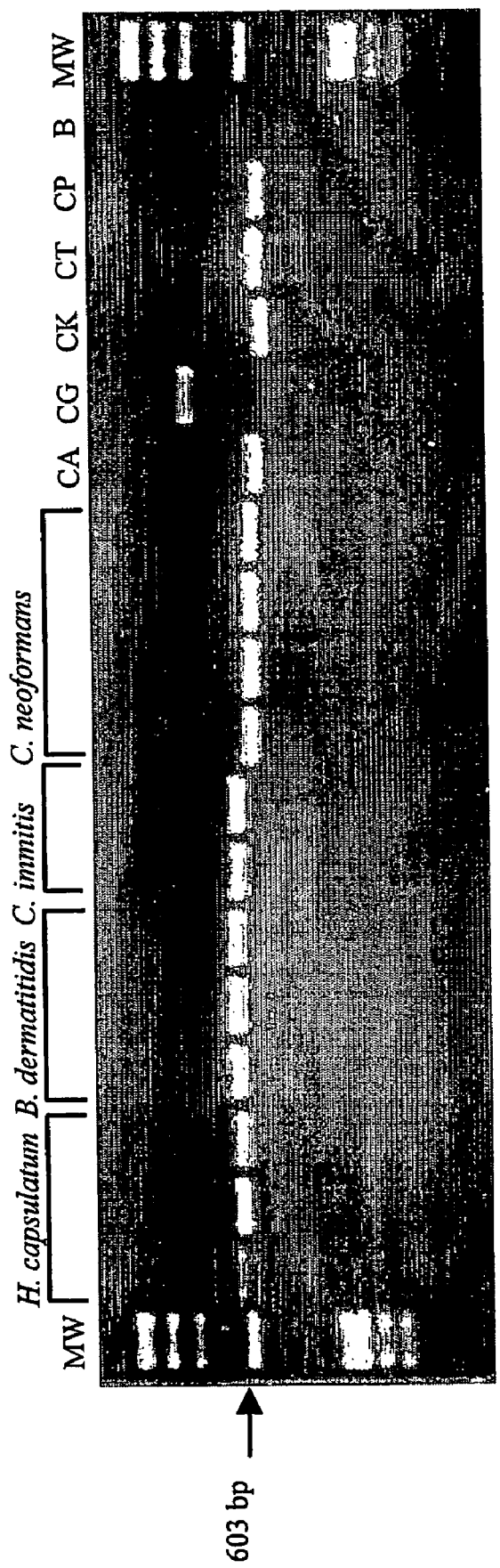
FIG. 7 is a digital image of PCR products amplified from fungal DNA and separated by size on an agarose gel.

The amplification of the rRNA gene using the ITS1 and ITS4 primers resulted in an approximately 600 bp amplicon for all fungi tested. As illustrated in FIG. 7, the molecular sizes of amplicons were especially similar among the dimorphic fungi. In FIG. 7, lane abbreviations are (from left to right): MW, molecular wt markers (HaeIII digest of φX174 plasmid, Roche, Indianapolis, Ind.); *H. capsulatum*, DNA amplified from *H. capsulatum* strains B293 (var. *duboisii*), Down's, and Fls-1; *B. dermatitidis*, DNA amplified from *B. dermatitidis* strains 4478, KL1, and A2; *C. immitis*, DNA amplified from *C. immitis* strains C635 and C735; *C. neoformans*, DNA amplified from *C. neoformans* strains 9759-MU-1 (serotype A), BIH409 (serotype B), K24066TAN (serotype C), and 9375 (serotype D); lanes CA, CG, CK, CT, and CP, DNA amplified from *C. albicans* (strain B311), *C. glabrata* (CDC Y-65), *C. krusei* (CDC 259-75), *C. tropicalis* (strain CDC 38), and *C. parapsilosis* (ATCC 22019), respectively; lane B, water blank (negative control). The greatest differences in amplicon size were observed among the five *Candida* species tested and were particularly pronounced for *C. glabrata* and *C. krusei* compared to all other *Candida* species. However, specific identification of the fungi using amplicon size alone was not possible and is not generally recommended. Podzorski, R. P., and D. H. Persing, In P. R. Murray, et al. (eds.), Manual of Clinical Microbiology, 6th ed.

(ASM Press, Washington, D.C., 1995), 130-157. Therefore, probes were designed to specifically identify each fungus using the PCR-EIA identification method described in Example 8.

Example 8

Polymerase Chain Reaction-Enzyme Immunoassay (PCR-EIA)

EIA identification of PCR products was performed as described in Elie, C. M., et al., J. Clin. Microbiol. 36:3260-65 (1998) and Fujita, S., et al., J. Clin. Microbiol. 33:962-7 (1995), with minor modifications. FIGS. 1A-B illustrate this protocol. Briefly, tubes containing 10 μl of heat-denatured (5 min at 95° C.) PCR amplicons were placed on ice, and 200 μl of hybridization buffer (4×SSC, pH 7.0, 0.02M HEPES, 0.002M EDTA, 0.15% Tween 20) containing 10 ng of ITS3-B and 10 ng of a digoxigenin-labeled specific probe was added. Samples were mixed and incubated at 37° C. for 1 h. One hundred microliters of the mixture was added in duplicate to each well of a streptavidin-coated, 96-well, microtiter plate (Roche) and incubated at ambient temperature for 1 h on a microtiter plate shaker (~350 rpm, Labline Instruments, Melrose Park, Ill.). Microtiter plates were washed 6 times with 0.01 M phosphate buffered saline, pH 7.2 (GibcoBRL, Life Technologies, Grand Island, N.Y.), containing 0.05% Tween 20 (Sigma Chemical Co., St Louis, Mo.) (PBST) before adding 100 μl of a 1:1000 dilution of horseradish peroxidase-labeled, anti-digoxigenin antibody (150 U/ml, Roche) per well. Plates were incubated for 1 h at ambient temperature with shaking and then washed 6 times with PBST. 3,3',5,5'-Tetramethylbenzidine (TMB)-$H_2O_2$ substrate (Kirkegaard and Perry, Gaithersburg, Md.) was then added to the wells and the color reaction was allowed to develop at ambient temperature for 15 min. The optical density of each well was immediately read at a wavelength of 650 nm in a UVMax microtiter plate reader (Molecular Devices, Sunnyvale, Calif.). The optical density of the duplicate wells were averaged and used in the analysis of the results. The optical density results were then converted to an EIA index (EI) which was calculated by dividing the optical density value of the wells which had received test DNA by the optical density of the PCR water control: O.D. of test DNA/O.D. of water blank=EI.

Example 9

Statistical Analysis

Student's t test was used to determine differences between the mean EI of probe hybridization to homologous and heterologous DNA. Differences were considered significant when the value of P was less than or equal to 0.05.

Example 10

Probe Specificity

Digoxigenin-labeled probes directed to the ITS2 region of rDNA were designed to specifically detect PCR amplicons from the most medically important yeast-like fungi. In addition to the microbe-specific probes, a probe was also designed as a primary screening probe (Dm; SEQ ID NO: 4) with which to identify only the systemic, dimorphic fungal pathogens. The specificity of these probes was confirmed using the PCR-EIA method in a checkerboard pattern as shown in Table 2.

TABLE 2

Specificity of oligonucleotide probes to DNA from yeast-like fungi

| | Mean EI ± S.E. (n) using DNA from: | | | | | | | | |
|---|---|---|---|---|---|---|---|---|---|
| PROBE | H. capsulatum | B. dermatitidis | C. immitis | P. brasiliensis | P. marneffei | S. schenckii | C. neoformans[b] | P. carinii | Candida species[c] |
| Dm | 11.0 ± 1.1 (34) | 9.4 ± 1.4 (24) | 16.9 ± 2.2 (14) | 13.9 ± 1.1 (21) | 3.0 ± 0.5 (31) | 0[d] | 0 | 0 | 0 |
| Hc | 15.8 ± 1.4 (37) | 0 | 0 | 0 | 0 | 0 | 0 | 0 | 0 |
| Bd | 0 | 11.9 ± 2.0 (20) | 4.3 ± 0.8 (10) | 0 | 0 | 0 | 0 | 0 | 0 |
| Ci | 0 | 0 | 21.9 ± 3.2 (13) | 0 | 0 | 0 | 0 | 0 | 0 |
| Pb | 0 | 0 | 0 | 10.8 ± 0.8 (22) | 0 | 0 | 0 | 0 | 0 |
| Pm | 0 | 0 | 0 | 0 | 7.6 ± 0.6 (36) | 0 | 0 | 0 | 0 |
| Ss | 0 | 0 | 0 | 0 | 0 | 23.6 ± 4.3 (12) | 0 | 0 | 0 |
| Cn | 0 | 0 | 0 | 0 | 0 | 0 | 42.7 ± 2.7 (31) | 0 | 0 |
| Pc | 0 | 0 | 0 | 0 | 0 | 0 | 0 | 6.2 ± 2.7 (10) | 0 |

[a]See Table 1 for definition of abbreviations.
[b]Includes DNA from serotypes A, B, C, and D.
[c]*Candida* species included: *C. albicans, C. glabrata, C. krusei, C. tropicalis,* and *C. parapsilosis*; excludes results for Hc probe against *C. albicans*: mean EI ± S.E. = 6.5 ± 1.0, (n = 10).
[d]A value of zero was assigned for all EI values less than 1.75 for ease of presentation. Mean EIA ± S.E. (n) for all heterologous DNA tested with the following probes: Dm, 1.13 ± 0.04 (n = 89); Hc, 1.2 ± 0.3 (n = 118); Bd, 1.41 ± 0.12 (n = 103); Ci, 1.0 ± 0.01 (n = 96); Pb, 1.01 ± 0.02 (n = 88); Pm, 0.99 ± 0.02 (n = 98); Ss, 0.99 ± 0.01 (n = 103); Cn, 0.98 ± 0.01 (n = 95); and Pc, 0.98 ± 0.01 (n = 96). All probes significantly hybridized to homologous DNA but not heterologous DNA at P < 0.001 except for Pc (P < 0.05) and Bd vs. *C. immitis* DNA (P < 0.01).

The dimorphic screening probe (Dm) successfully hybridized with PCR amplicons from all strains of the major systemic, dimorphic fungi tested (*H. capsulatum, B. dermatiti-* dis, *C. immitis, P. brasiliensis*, and *P. marneffei*) but not with DNA from any strain of the other yeast-like fungi (*S. schenckii, C. neoformans, Canidida* species or *P. carinii*).

Microbe-specific probes (Hc, Bd, Ci, Pb, Pm, Ss, Cn, and Pc), designed to detect only DNA amplified from their homologous fungus, were tested against PCR amplicons from all strains of both homologous as well as heterologous yeast-like fungi. The results in Table 2 demonstrate that the microbe-specific probes hybridized with DNA from homologous fungi and not with DNA from heterologous fungi (P<0.001 or P<0.05) with minor exceptions. There was some reactivity of the *B. dermatitidis* probe observed when it was tested against *C. immitis* DNA. However, the hybridization signal for the *B. dermatitidis* probe tested against *B. dermatitidis* DNA was statistically greater than that for *C. immitis* DNA (11.9±2.0 versus 4.3±0.8, P <0.01). In addition, the reverse (i.e., the *C. immitis* probe tested against *B. dermatitidis* DNA) was negative and could be used to differentiate the two fungi by a process of elimination. There was also a hybridization signal observed for the *H. capsulatum* probe reacted with DNA from *C. albicans* (15.8±1.4 versus 6.5±1.0, P<0.001), but no signal was observed for any of the other *Candida* species tested using this probe. The dimorphic probe, however, did not hybridize with *C. albicans* DNA and the *C. albicans* probe does not hybridize with *H. capsulatum* DNA (data not shown; see Elie, et al., and Fujita, et al.).

Example 11

Confirmation of Probe Specificity using Multiple Strains of Homologous and Heterologous Fungi To further analyze each probe's capacity to hybridize with only DNA from homologous fungi, DNA from multiple strains of each of the systemic dimorphic fungi were tested in the PCR-EIA. Results are shown in Table 3.

TABLE 3

Reactivity of oligonucleotide probes to dimorphic pathogens against DNA from multiple strains of homologous and heterologous dimorphic fungi.

| | Mean EI ± S.E.(n) using DNA from[a]: | | | | | | |
|---|---|---|---|---|---|---|---|
| | *H. capsulatum* isolates | | | | *B. dermatitidis* isolates | | |
| PROBE[b] | 1 | 2 | 3 | 4 | 1 | 2 | 3 |
| Dm | 13.7 ± 2.8 (8) | 8.8 ± 1.8 (7) | 10.3 ± 2.0 (11) | 11.4 ± 2.8 (8) | 9.2 ± 1.8 (9) | 12.5 ± 3.0 (9) | 4.9 ± 0.8 (6) |
| Hc | 17.3 ± 3.8 (9) | 15.1 ± 2.3 (6) | 15.8 ± 2.6 (10) | 14.7 ± 2.6 (9) | 0[c] | 0 | 0 |
| Bd | 0 | 0 | 0 | 0 | 9.7 ± 2.4 (6) | 15.4 ± 3.5 (9) | 8.3 ± 3.3 (5) |
| Ci | 0 | 0 | 0 | 0 | 0 | 0 | 0 |
| Pb | 0 | 0 | 0 | 0 | 0 | 0 | 0 |

| | Mean EI ± S.E.(n) using DNA from[a]: | | | | |
|---|---|---|---|---|---|
| | *C. immitis* isolates | | *P. brasiliensis* isolates | | |
| PROBE[b] | 1 | 2 | 1 | 2 | 3 |
| Dm | 14.8 ± 1.8 (6) | 18.5 ± 3.6 (8) | 13.3 ± 2.2 (7) | 14.1 ± 2.3 (7) | 14.3 ± 2.0 (6) |
| Hc | 0 | 0 | 0 | 0 | 0 |
| Bd | 4.7 ± 1.2 (5) | 3.8 ± 1.2 (5) | 0 | 0 | 0 |
| Ci | 23.8 ± 4.2 (6) | 20.2 ± 4.9 (7) | 0 | 0 | 0 |
| Pb | 0 | 0 | 9.4 ± 1.5 (7) | 12.3 ± 1.4 (7) | 12.0 ± 0.4 (6) |

[a]Isolates used: *H. capsulatum*: 1) G186B, 2) B293, 3) Downs, 4)FLs1; *B. dermatitidis*: 1) 4478, 2) A2, 3) KL-1; *C. immitis*: 1) C634, 2) C735; *P. brasiliensis*: 1) Pb18, 2) rh, 3) soil.
[b]See Table 1 for definition of abbreviations.
[c]A value of zero was assigned for all EI values less than 1.75 for ease of presentation. Mean EI ± S.E. (n) for heterologous DNA tested with the following probes: Hc, 1.2 ± 0.05 (n = 42); Bd, 1.74 ± 0.27 (n = 44); Bd without Ci DNA 0.99 ± 0.02 (n = 34); Ci, 1.0 ± 0.02 (n = 42); and Pb, 0.99 ± 0.03 (n = 33). All probes significantly hybridized to homologous DNA but not heterologous endemic dimorphic DNA at P < 0.001

The probe designed to identify all systemic dimorphic fungi (Dm) hybridized with DNA from all strains of *H. capsulatum, B. dermatitidis, C. immitis,* and *P. brasiliensis* tested. In addition, the probes specific for individual dimorphic fungi (Hc, Bd, Ci, Pb) hybridized only to DNA isolated from homologous fungi, but not DNA isolated from heterologous fungi. The minor hybridization signal observed for the *B. dermatitidis* probe tested against *C. immitis* DNA was similar for both strains of *C. immitis* tested.

Example 12

Sensitivity of Probes using the PCR-EIA Method

Figure 6:
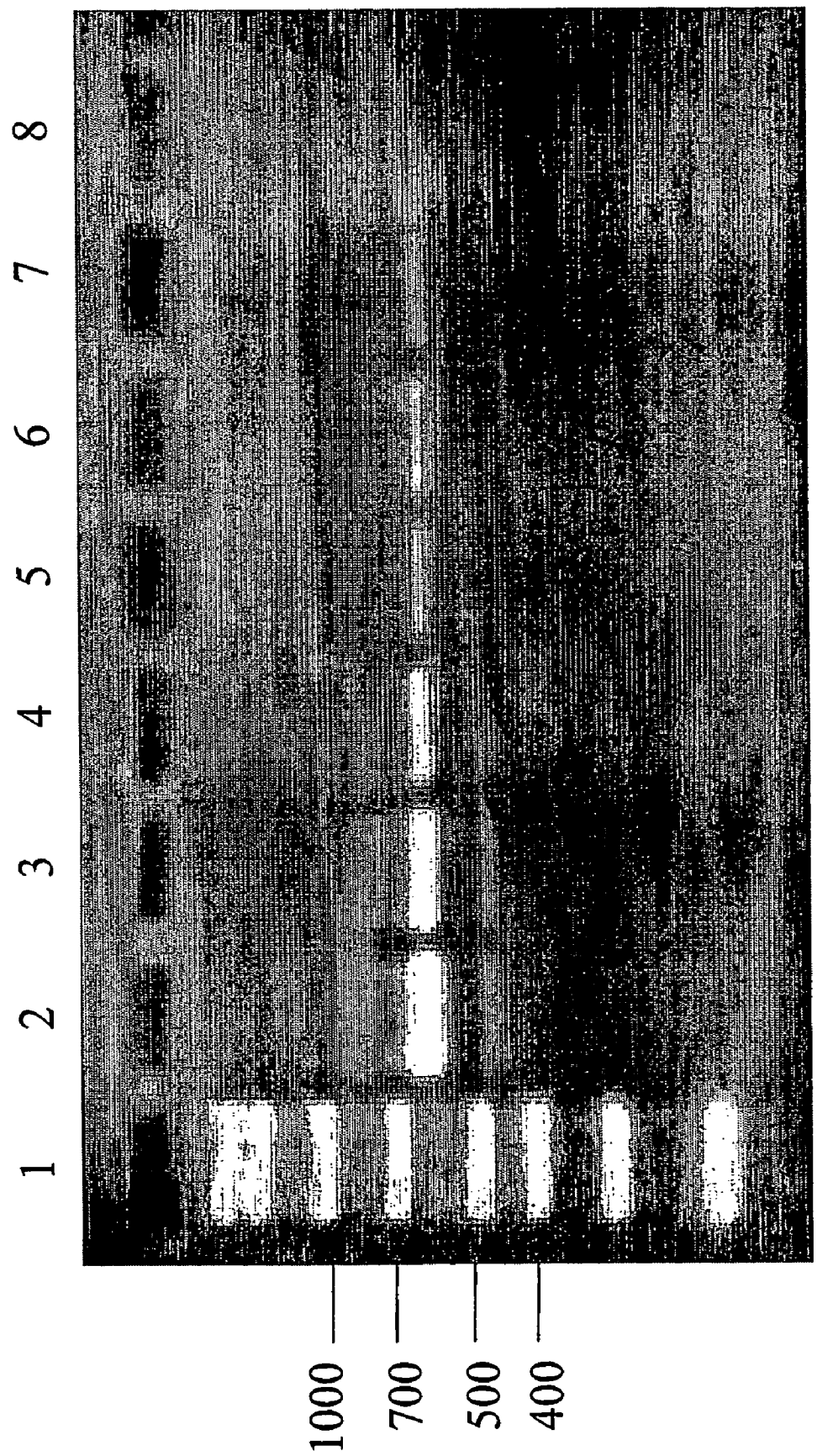
FIG. 6 is a digital image of an agarose gel demonstrating detection of amplicons separated via gel electrophoresis.

To assess the limit of sensitivity of the PCR-EIA method, compared to that for detection of amplicons by agarose gel electrophoresis, *H. capsulatum* (Down's strain) DNA was serially diluted prior to PCR amplification and then assessed by both agarose gel electrophoresis and PCR-EIA. FIG. 6 is a digital print of an agarose gel, stained with ethidium bromide, demonstrating detection of amplicons at a concentration as low as 16 pg of DNA. In FIG. 6, lane 1 contains molecular size markers (AmpliSize molecular ruler, BioRad, Hercules, Calif.); lanes 2 to 8, pg of DNA per reaction: 20,000; 10,000; 2,000; 400; 80; 16; and 3.2, respectively. In contrast, as little as 3.2 pg of DNA could be detected by PCR-EIA as demonstrated in Table 4.

TABLE 4

Evaluation of the sensitivity of the PCR-EIA assay.

| DNA conc[a] | EIA Index[b] | Agarose gel[c] |
|---|---|---|
| 10,000 | 53.3 | + |
| 2,000 | 50.4 | + |
| 400 | 38.2 | + |
| 80 | 13.9 | + |
| 16 | 5.3 | + |
| 3.2 | 2.2 | − |
| 0.64 | 1.53 | − |
| 0.128 | 1.15 | − |
| 0.0256 | 1.06 | − |

[a]pg/reaction
[b]EIA index using *H. capsulatum* (Downs strain) DNA
[c]+ = visually positive band in gel after EtBr staining Example 13

Differentiation of *Penicillium marneffei*

Microorganisms

Clinical isolates, or cultures obtained from the American Type Culture Collection (ATCC), or the CDC Mycotic Diseases Branch Laboratory, were used. See Table 5 below.

DNA Isolation

DNA was extracted from all species by using the FastDNA kit (Q-BIOgene, Carlsbad, Calif.) with minor modification.

Design of Probes

Universal fungal primers, ITS3 and ITS4, were used to amplify the ITS2 rDNA region. Oligonucleotide probes were designed from GenBank sequence data for the ITS2 region of *Penicillium* species, or were sequenced by standard capillary methods if sequences were not available in GenBank.

PCR Amplification

The reaction mixture contained 5 μl of 10× PCR buffer, 0.2 μM dNTPs, 0.5 μl of each primer (20 μM), Taq DNA polymerase (2.5 U, Roche), template DNA (5 ng), and sterile distilled water to bring the volume to 50 μl. PCR amplification conditions were 5 min of denaturation at 95° C., followed by 30 cycles of 95° C. for 30 s, 58° C. for 30 s, and 72° C. for 1 min, carried out on a Perkin-Elmer thermal cycler described above. A final extension step of 72° C. for 5 min was then conducted. Electrophoresis was carried out at 80 V for approximately 1 h in gels composed of 1% (wt/vol) agarose. Gels were stained with ethidium bromide, visualized with a UV transilluminator, and photographed.

EIA

PCR-amplified DNA was hybridized to species-specific digoxigenin-labeled probes and a universal biotinylated probe, and then the complex was added to streptavidin-coated microtitration plates and captured. A colorimetric EIA was then conducted to detect captured DNA by using horseradish peroxidase-conjugated anti-digoxigenin antibody and TMB-$H_2O_2$ substrate, as illustrated in FIGS. 1A-B.

Statistical Analyses

Student's t test was used to determine significant differences between mean absorbance values of homologous and heterologous DNA reactions with probes. Differences were considered significant when the value of P was less than or equal to 0.05.

TABLE 5

Source and characteristics of isolates.

| Isolate | Identification Number | Source/Characteristics |
|---|---|---|
| *Penicillium* spp. | | |
| *P. marneffei* | ATCC 18224 | Type culture, isolated from bamboo rat |
| *P. marneffei* | B6006 | CDC, CSF from AIDS patient |
| *P. marneffei* | B6015 | CDC, human skin biopsy |
| *P. marneffei* | JH05 | Gift from W. Merz, human skin lesion |
| *P. marneffei* | B6010 | CDC |
| *P. camembertii* | ATCC 4845 | Camembert cheese, France |
| *P. caseicolum* | ATCC 6986 | Camembert cheese |
| *P. chrysogenum* | ATCC 10106 | Produces chrysogenin |
| *P. citrinum* | B5809 | CDC |
| *P. glabrum* | ATCC 16349 | Production of acid protease |
| *P. griseofulvum* | ATCC 66967 | Penicilliosis patient |
| *P. italicum* | ATCC 48114 | From fruit |
| *P. janthinellum* | ATCC 10069 | Soil |
| *P. purpurescens* | ATCC 20075 | Soil |
| *P. purpurogenum* | ATCC 10064 | Unknown |
| *P. roquefortii* | ATCC 10110 | Roquefort cheese, France |
| *P. rubefaciens* | ATCC 48481 | Soil |
| *P. spinulosum* | ATCC 16348 | Tanning liquor |
| *Aspergillus* spp. | | |
| *A. flavus* | ATCC 64025 | Human sputum |
| *A. fumigatus* | ATCC 42202 | Human sputum |
| *A. nidulans* | ATCC 10074 | Unknown |
| *A. niger* | ATCC 16888 | Tannin-gallic acid fermentation |
| *A. terreus* | ATCC 1012 | Soil |
| *Candida* spp. | | |
| *C. albicans* | CBS 2730 | Gift from R. Rüchel (laboratory variant) |
| *C. glabrata* | CDC Y65 | CDC |
| *C. krusei* | CDC 259-75 | CDC |
| *C. parapsilosis* | CDC 22019 | CDC |
| *C. tropicalis* | CDC 38 | CDC |
| *Fusarium* spp. | | |
| *F. moniliforme* | ATCC 38159 | Human cutaneous infection |
| *F. oxysporum* | ATCC 4254 | Unknown |
| *F. solani* | ATCC 52628 | Unknown |
| *Mucor* spp. | | |
| *M. circinelloides* | ATCC 1209B | Minus strain |
| *M. indicus* | ATCC 4857 | Unknown |
| *M. plumbeus* | ATCC 4740 | Unknown |
| *M. racemosus* | ATCC 22365 | Forest soil under basswood tree |
| *M. rouxii* | ATCC 24905 | Rice fermentations |
| *Rhizopus* spp. | | |
| *R. circinans* | ATCC 34101 | Peach |
| *R. microsporus* | ATCC 14050 | Fatal human infection |
| *R. oryzae* | ATCC 34965 | Pus from sinus (transplant recipient) |
| *R. stolonifer* | ATCC 14037 | Zygospore germination |
| Other genera | | |
| *Apophysomyces elegans* | ATCC 46557 | Human bronchial washing |
| *Blastomyces dermatitidis* | ATCC 60915 | Attenuated mutant from human |

TABLE 5-continued

Source and characteristics of isolates.

| Isolate | Identification Number | Source/Characteristics |
|---|---|---|
| Neosartorya fischeri | ATCC 66781 | Frozen pineapple juice concentrate |
| Pseudallescheria boydii | ATCC 36282 | Human lung |
| Sporothrix schenckii | ATCC 28184 | Human arm lesion |

TABLE 6

Specificity of P. marneffei probe versus DNAs from 13 Penicillium species

| Species | Mean absorbance$_{650\ nm}$ ± S.E. [a] |
|---|---|
| P. marneffei | 1.979 ± 0.087 (15) [b] |
| P. camembertii | 0.001 ± 0.001 (3) |
| P. caseicolum | 0.001 ± 0.001 (3) |
| P. chrysogenum | 0.020 ± 0.003 (3) |
| P. glabrum | 0.017 ± 0.001 (3) |
| P. griseofulvum | 0.005 ± 0.002 (3) |
| P. italicum | 0.010 ± 0.001 (3) |
| P. janthinellum | 0.009 ± 0.004 (3) |
| P. purpurescens | 0.005 ± 0.002 (3) |
| P. purpurogenum | 0.001 ± 0.001 (3) |
| P. roquefortii | 0.004 ± 0.003 (3) |
| P. rubefaciens | 0.020 ± 0.001 (3) |
| P. spinulosum | 0.001 ± 0.000 (3) |

[a] Each sample was prepared and tested in at least three separate experiments. The P. marneffei probe hybridized to its homologous species DNA but not to heterologous species DNA (P < 0.001). Mean absorbance $_{650\ nm}$ ± S.E. for all non-P. marneffei Penicillium species = 0.008 ± 0.007 (n = 36). Negative control water blank was subtracted from all samples.
[b] Mean absorbance $_{650\ nm}$ ± S.E. for 5 strains of P. marneffei tested in three separate experiments.

TABLE 7

Specificity of P. marneffei probe versus DNAs from non-Penicillium genera
Mean absorbance $_{650\ nm}$ ± S.E.[a]

| Target DNA [b] | P. marneffei | Aspergillus spp | Fusarium spp | Mucor spp | Rhizopus spp |
|---|---|---|---|---|---|
| P. marneffei (n = 3) | 1.24 ± 0.12 | 0 [c] | 0 | 0 | 0 |
| Aspergillus spp. (n= 5) | 0 | 1.67 ± 0.20 | 0 | 0 | 0 |
| Fusarium spp. (n = 3) | 0 | 0 | 1.28 ± 0.31 | 0 | 0 |
| Mucor spp. (n = 5) | 0 | 0 | 0 | 1.85 ± 0.10 | 0 |
| Rhizopus spp. (n = 4) | 0 | 0 | 0 | 0 | 1.64 ± .33 |
| All other fungi (n = 10) | 0 | 0 | 0 | 0 | 0 |

[a] Each sample was prepared and tested in at least two separate experiments. Each probe specifically hybridized to its homologous DNA but not to heterologous DNA (P < 0.001). Negative control water blank was subtracted from all samples.
[b] Target DNA was derived from the number of different isolates (P. marneffei) or species in parentheses; species included those from Mucor (M. circinelloides f circinelloides, M. indicus, M. plumbeus, M. racemosus, and M. rouxii), Rhizopus (R. circinans, R. microsporus, and R. oryzae), Aspergillus (A. flavus, A. fumigatus, A. nidulans, A. niger, and A. terreus), Fusarium (F. moniliforme, F. oxysporum, and F. solani), and all other fungi (C. albicans, C. glabrata, C. krusei, C. parapsilosis, C. tropicalis, B. dermatitidis, P. boydii, S. schenckii, N. fischeri, and A. elegans).
[c] A value of zero was assigned for all mean absorbance values of less than 0.01 for ease of presentation.

TABLE 8

Specificity of Penicillium species probes versus DNAs from other fungi
Mean absorbance$_{650\ nm}$ ± S.E. [a]

| | Probes for: | | |
|---|---|---|---|
| Target DNA | P. marneffei | P. purpurogenum | P. citrinum |
| P. marneffei | 1.635 ± 0.021 | 0 [b] | 0 |
| P. purpurogenum | 0 | 0.434 ± 0.009 | 0 |
| P. camembertii | 0 | 0.198 ± 0.005 | 0 |
| P. citrinum | 0 | 0 | 0.846 ±0.001 |
| P. caseicolum | 0 | 0 | 0 |
| P. chrysogenum | 0 | 0 | 0 |
| P. glabrum | 0 | 0 | 0 |
| P. griseofulvum | 0 | 0 | 0 |
| P. italicum | 0 | 0 | 0 |
| P. purpurescens | 0 | 0 | 0 |
| P. roquefortii | 0 | 0 | 0 |
| A. fumigatus | 0 | 0 | 0 |
| C. albicans | 0 | 0 | 0 |
| F. solani | 0 | 0 | 0 |
| M. racemosus | 0 | 0 | 0 |
| P. boydii | 0 | 0 | 0 |
| S. schenckii | 0 | 0 | 0 |

[a] Each sample was prepared and tested in at least two separate experiments. Each probe hybridized to homologous DNA but not to heterologous DNA (P < 0.001) with the exception of the P. purpurogenum probe with P. camembertii DNA. Negative control water blank was subtracted from all samples.
[b] A value of zero was assigned for all mean absorbance values of less than 0.03 for ease of presentation.

Having illustrated and described the principals of the invention by several embodiments, it should be apparent that those embodiments can be modified in arrangement and detail without departing from the principles of the invention. Thus, the invention includes all such embodiments and variations thereof, and their equivalents.

We claim:

1. A method of detecting the presence of any of the dimorphic fungal pathogens *H. capsulatum, B. dermatitidis, C. immitis, P. brasiliensis,* and/or *P. marneffei* in a sample, comprising the steps of:

contacting the sample with a dimorphic probe, wherein the dimorphic probe specifically detects the dimorphic fungal pathogens *H. capsulatum, B. dermatitidis, C. immitis, P. brasiliensis,* and *P. marneffei,* and comprises at least 15 contiguous nucleotides of SEQ ID NO: 4 or at least 15 contiguous nucleotides of nucleotides 1-25 of any of SEQ ID NOs: 14-17, wherein under the conditions employed in the contacting step, said dimorphic probe hybridizes to ITS2 nucleic acids of each of *H.*

*capsulatum, B. dermatitidis, C. immitis, P. brasiliensis,* and *P. marneffei* if said ITS2 nucleic acids are present in the sample, and wherein under the conditions employed in the contacting step, said dimorphic probe does not hybridize to ITS2 nucleic acids of each of *S. schenckii, C. neoformans, C. albicans,* and *P. carinii;* and detecting hybridization between the dimorphic probe and fungal ITS2 nucleic acids present in the sample, wherein detection of hybridization indicates the presence of one or more of said dimorphic fungal pathogens in the sample.

2. The method of claim 1, wherein the sample is a biological or environmental sample.

3. The method of claim 1, wherein the sample comprises DNA isolated from a biological or environmental sample.

4. The method of claim 1, wherein the sample comprises fungal ITS2 nucleic acids produced by a further step of polymerase chain reaction or polymerase chain reaction-enzyme immunoassay.

5. The method of claim 4, wherein a primer comprising SEQ ID NO: 1, SEQ ID NO: 2, or SEQ ID NO: 3 is used in the polymerase chain reaction or polymerase chain reaction-enzyme immunoassay.

6. The method of claim 5, wherein a primer consisting of SEQ ID NO: 1, SEQ ID NO: 2, or SEQ ID NO: 3 is used in the polymerase chain reaction or polymerase chain reaction-enzyme immunoassay.

7. The method of claim 1, further comprising:
detecting hybridization between a second probe and fungal ITS2 nucleic acids present in the sample, wherein the second probe is a species-specific probe that differentiates a species of fungus from another species of fungus in the same genus, or a microbe-specific probe that differentiates a species of fungus from another species of fungus in a different genus.

8. The method of claim 7, wherein the second probe comprises at least 15 contiguous nucleotides of SEQ ID NO: 5, SEQ ID NO: 6, SEQ ID NO: 7, or SEQ ID NO: 8.

9. The method of claim 8, wherein the second probe comprises at least 20 contiguous nucleotides of SEQ ID NO: 5, SEQ ID NO: 6, SEQ ID NO: 7, or SEQ ID NO: 8.

10. The method of claim 9, wherein the second probe comprises SEQ ID NO: 5, SEQ ID NO: 6, SEQ ID NO: 7, or SEQ ID NO: 8.

11. The method of claim 10, wherein the second probe consists of SEQ ID NO: 5, SEQ ID NO: 6, SEQ ID NO: 7, or SEQ TD NO: 8.

12. The method of claim 1, wherein the dimorphic probe comprises at least 15 contiguous nucleotides of SEQ ID NO: 4.

13. The method of claim 12, wherein the dimorphic probe comprises at least 20 contiguous nucleotides of SEQ ID NO: 4.

14. The method of claim 13, wherein the dimorphic probe comprises SEQ ID NO: 4.

15. The method of claim 14, wherein the dimorphic probe consists of SEQ ID NO: 4.

16. The method of claim 1, wherein the step of detecting hybridization comprises detecting a label on the dimorphic probe.

17. The method of claim 16, wherein the label comprises a radioactive isotope, an enzyme substrate, a co-factor, a ligand, a chemiluminescent agent, a fluorescent agent, a hapten, or an enzyme.

18. A method of differentiating the dimorphic fungal parhogens *H. capsulatum, B. dermatitidis, C. immitis, P. brasiliensis,* and *P. marneffei* from other dimorphic fungi and non-dimorphic fungi, comprising the steps of:

contacting a sample comprising fungal nucleic acids with a dimorphic probe, wherein the dimorphic probe specifically detects the dimorphic fungal pathogens *H. capsulatum, B. dermatitidis, C. immitis, P. brasiliensis,* and *P. marneffei,* and comprises at least 15 contiguous nucleotides of SEQ ID NO: 4 or at least 15 contiguous nucleotides of nucleotides 1-25 of any of SEQ ID NOs: 14-17, wherein under the conditions employed in the contacting step, said dimorphic probe hybridizes to ITS2 nucleic acids of each of *H. capsulatum, B. dermatitidis, C. immitis, P. brasiliensis,* and *P. marneffei* if said ITS2 nucleic acids are present in the sample, and wherein under the conditions employed in the contacting step, said dimorphic probe does not hybridize to ITS2 nucleic acids of each of *S. schenckii, C. neoformans, C. albicans,* and *P. carinii;* and detecting hybridization between the dimorphic probe and fungal ITS2 nucleic acids present in the sample, wherein detection of hybridization indicates the presence of one or more of said dimorphic fungal pathogens in the sample, and an absence of detection of hybridization indicates the presence of a non-dimorphic fungus or other dimorphic fungus in the sample.

19. The method of claim 18, wherein the sample is a biological or environmental sample.

20. The method of claim 18, wherein the sample comprises DNA isolated from a biological or environmental sample.

21. The method of claim 18, wherein the sample comprises fungal ITS2 nucleic acids produced by a further step of polymerase chain reaction or polymerase chain reaction-enzyme immunoassay.

22. The method of claim 21, wherein a primer comprising SEQ ID NO: 1, SEQ ID NO: 2, or SEQ ID NO: 3 is used in the polymerase chain reaction or polymerase chain reaction-enzyme immunoassay.

23. The method of claim 22, wherein a primer consisting of SEQ ID NO: 1, SEQ ID NO: 2, or SEQ ID NO: 3 is used in the polymerase chain reaction or polymerase chain reaction-enzyme immunoassay.

24. The method of claim 18, further comprising:
detecting hybridization between a second probe and fungal ITS2 nucleic acids present in the sample, wherein the second probe is a species-specific probe that differentiates a species of fungus from another species of fungus in the same genus, or a microbe-specific probe that differentiates a species of fungus from another species of fungus in a different genus.

25. The method of claim 24, wherein the second probe comprises at least 15 contiguous nucleotides of SEQ ID NO: 5, SEQ ID NO: 6, SEQ ID NO: 7, or SEQ ID NO: 8.

26. The method of claim 25, wherein the second probe comprises at least 20 contiguous nucleotides of SEQ ID NO: 5, SEQ ID NO: 6, SEQ ID NO: 7, or SEQ ID NO: 8.

27. The method of claim 26, wherein the second probe comprises SEQ ID NO: 5, SEQ ID NO: 6, SEQ ID NO: 7. or SEQ ID NO: 8.

28. The method of claim 27, wherein the second probe consists of SEQ ID NO: 5. SEQ ID NO: 6, SEQ ID NO: 7, or SEQ ID NO: 8.

29. The method of claim 18, wherein the dimorphic probe comprises at least 15 contiguous nucleotides of SEQ ID NO: 4.

30. The method of claim 29, wherein the dimorphic probe comprises at least 20 contiguous nucleotides of SEQ ID NO: 4.

31. The method of claim 30, wherein the dimorphic probe comprises SEQ ID NO: 4.

32. The method of claim 31, wherein the dimorphic probe consists of SEQ ID NO: 4.

33. The method of claim 18, wherein the step of detecting hybridization comprises detecting a label on the dimorphic probe.

34. The method of claim 33, wherein the label comprises a radioactive isotope, an enzyme substrate, a co-factor, a ligand, a chemiluminescent agent, a fluorescent agent, a hapten, or an enzyrne.

* * * * *